(12) United States Patent
Shigeta et al.

(10) Patent No.: US 8,654,333 B2
(45) Date of Patent: Feb. 18, 2014

(54) SURFACE INSPECTION APPARATUS AND METHOD

(75) Inventors: Bungo Shigeta, Kanagawa (JP); Ippei Takahashi, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 391 days.

(21) Appl. No.: 13/070,565

(22) Filed: Mar. 24, 2011

(65) Prior Publication Data

US 2011/0242537 A1     Oct. 6, 2011

(30) Foreign Application Priority Data

Mar. 30, 2010   (JP) .................................. 2010-077901
Mar. 30, 2010   (JP) .................................. 2010-077902

(51) Int. Cl.
  *G01N 21/84*   (2006.01)
  *G01N 21/00*   (2006.01)

(52) U.S. Cl.
  USPC ........................................ 356/430; 356/432

(58) Field of Classification Search
  USPC ................ 356/237.1–241.6, 242.1–243.8,
               356/426–431, 600–640
  See application file for complete search history.

(56) References Cited

U.S. PATENT DOCUMENTS

| | | | | |
|---|---|---|---|---|
| 3,135,867 A | * | 6/1964 | Daneff ........................... | 356/431 |
| 3,859,538 A | * | 1/1975 | Mannonen ................ | 250/559.46 |
| 4,047,029 A | * | 9/1977 | Allport ........................... | 378/90 |
| 4,218,144 A | * | 8/1980 | Whitehouse et al. .......... | 356/446 |
| 4,318,129 A | * | 3/1982 | Zwirn ............................ | 348/678 |
| 4,570,074 A | * | 2/1986 | Jette .......................... | 250/559.49 |
| 4,675,730 A | * | 6/1987 | Adomaitis et al. ............. | 348/131 |
| 4,724,481 A | * | 2/1988 | Nishioka ........................ | 348/133 |
| 5,068,799 A | * | 11/1991 | Jarrett, Jr. ........................ | 702/40 |
| 5,104,523 A | * | 4/1992 | Masaharu et al. ............. | 209/585 |
| 5,164,603 A | * | 11/1992 | Hartman et al. .......... | 250/559.46 |
| 5,387,978 A | * | 2/1995 | Okafuji et al. ................ | 356/431 |

(Continued)

FOREIGN PATENT DOCUMENTS

| | | |
|---|---|---|
| JP | 05-215697 | 8/1993 |
| JP | 2004-271421 | 9/2004 |
| JP | 2008-298566 | 12/2008 |

OTHER PUBLICATIONS

Notification of Reasons for Refusal dated Jun. 26, 2013 issued by the Japanese Patent Office in Japanese Patent Application No. 2010-077901 with English translation, 4 pages.

*Primary Examiner* — Gregory J Toatley
*Assistant Examiner* — Jarreas C Underwood
(74) *Attorney, Agent, or Firm* — Young & Thompson

(57) ABSTRACT

A surface inspection apparatus includes a light source for applying a detection laser beam to a film sample. A light receiver has plural photomultiplier tubes arranged in a width direction of the film sample, for receiving output light reflected by the film sample. A defect detector detects a defect on the film sample according to an output signal output by each of the photomultiplier tubes. A sensitivity corrector sets sensitivity of the photomultiplier tubes to process an output of the light receiver for output noise suppression. Specifically, the sensitivity corrector determines a set sensitivity of the photomultiplier tubes by correcting a sensitivity characteristic thereof for abnormality detection, to keep a sensitivity difference between the photomultiplier tubes as small as a predetermined value or less. Furthermore, plural light valves upstream from the light receivers are controlled by the sensitivity corrector for their transmittance.

15 Claims, 22 Drawing Sheets

(56) References Cited

U.S. PATENT DOCUMENTS

| | | | |
|---|---|---|---|
| 5,440,648 A * | 8/1995 | Roberts et al. | 382/141 |
| 5,569,835 A * | 10/1996 | Kenney et al. | 73/1.81 |
| H1616 H * | 12/1996 | Wolfe | 348/88 |
| 5,642,198 A * | 6/1997 | Long | 356/430 |
| 5,696,591 A * | 12/1997 | Bilhorn et al. | 356/429 |
| 6,750,466 B2 * | 6/2004 | Guha et al. | 250/559.46 |
| 7,342,654 B2 * | 3/2008 | Laue et al. | 356/239.1 |
| 8,084,260 B2 * | 12/2011 | Gunstream et al. | 436/8 |

* cited by examiner

FIG. 4

| | | | | | | | | | | | | | | | | | | | | | | | |
|---|---|---|---|---|---|---|---|---|---|---|---|---|---|---|---|---|---|---|---|---|---|---|---|
| 21h | 68 | 93 | 88 | 90 | 79 | 71 | 86 | 97 | 68 | 93 | 88 | 90 | 79 | 71 | 86 | 97 | 68 | 93 | 88 | 90 | 79 | 71 | 86 | 97 |
| 21g | 83 | 100 | 94 | 95 | 91 | 82 | 89 | 90 | 83 | 100 | 94 | 95 | 91 | 82 | 89 | 90 | 83 | 100 | 94 | 95 | 91 | 82 | 89 | 90 |
| 21f | 97 | 98 | 93 | 86 | 82 | 85 | 86 | 82 | 97 | 98 | 93 | 86 | 82 | 85 | 86 | 82 | 97 | 98 | 93 | 86 | 82 | 85 | 86 | 82 |
| 21e | 98 | 99 | 87 | 79 | 75 | 81 | 86 | 79 | 98 | 99 | 87 | 79 | 75 | 81 | 86 | 79 | 98 | 99 | 87 | 79 | 75 | 81 | 86 | 79 |
| 21d | 95 | 98 | 83 | 71 | 69 | 72 | 77 | 71 | 95 | 98 | 83 | 71 | 69 | 72 | 77 | 71 | 95 | 98 | 83 | 71 | 69 | 72 | 77 | 71 |
| 21c | 96 | 94 | 76 | 66 | 65 | 63 | 66 | 61 | 96 | 94 | 76 | 66 | 65 | 63 | 66 | 61 | 96 | 94 | 76 | 66 | 65 | 63 | 66 | 61 |
| 21b | 81 | 77 | 62 | 60 | 58 | 54 | 58 | 50 | 81 | 77 | 62 | 60 | 58 | 54 | 58 | 50 | 81 | 77 | 62 | 60 | 58 | 54 | 58 | 50 |
| 21a | 75 | 72 | 64 | 62 | 63 | 59 | 65 | 52 | 75 | 72 | 64 | 62 | 63 | 59 | 65 | 52 | 75 | 72 | 64 | 62 | 63 | 59 | 65 | 52 |

7a, 7b, 7c, 21a

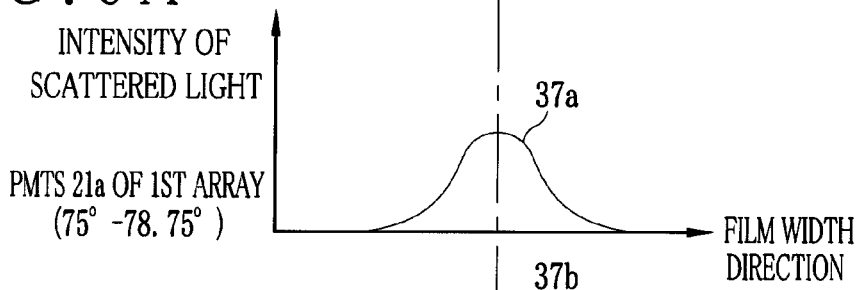
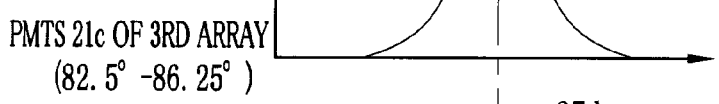
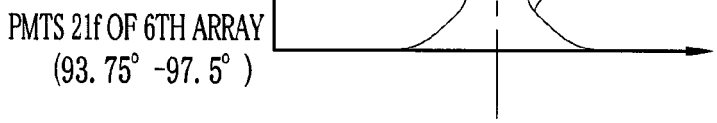
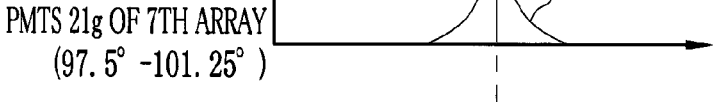

SURFACE INSPECTION APPARATUS AND METHOD

BACKGROUND OF THE INVENTION

1. Field of the Invention

The present invention relates to a surface inspection apparatus and method. More particularly, the present invention relates to a surface inspection apparatus and method in which precision in photoelectrically detecting defects can be high.

2. Description Related to the Prior Art

A surface inspection apparatus inspects a surface of a film sample traveling continuously, and detects defects. A light source in the surface inspection apparatus emits a detection laser beam to the film sample. Light receivers receive the detection laser beam transmitted or reflected by the film sample. If a defect is present on the film sample in a streak form or the like, the defect scatters the detection laser beam to create scattered light. The light receivers receive the scattered light, and generate an output signal from which the defect is detected. According to types of the defect, there are differences in a direction of scattering the scattered light at the defect. For example, a scratch defect has a streak form or elliptical form extending in a longitudinal direction of the film sample. The scattered light from the scratch defect scatters in a film width direction of the film sample.

According to the surface inspection apparatus and a sensor assembly of JP-A 5-215697, the light receivers are arranged in the longitudinal direction and the film width direction of the film sample. The defect on the film sample is detected according to a location of the light receivers of entry of the detection laser beam and light amount information of a light amount of the detection laser beam being received. Types of the defect are detected among a retracting defect and plane surface defect, and among various types of retracting defects, such as scratch defect, pit defect, crack defect and the like. For example, a scratch defect is detected if the detection laser beam is received by one of the light receivers positioned in the film width direction of the film sample.

A sensor array or multiple photomultiplier is available in the field of photo detection, and includes arrays of photomultiplier tubes. In JP-A 5-215697, the photomultiplier tubes are typically used in which the light receivers are arranged in both of the longitudinal direction and the film width direction of the film sample. Voltage for application for the photomultiplier tubes is equal in the multiple photomultiplier. There occurs a difference in sensitivity between the photomultiplier tubes. Even the scattered light of an equal light amount is received, differences will occur in the light amount information of the detection due to the sensitivity difference. Precision in the abnormality detection is considerably low.

In JP-A 5-215697, there is no discernment of the detection laser beam received by the light receivers among statuses including a main output beam normally reflected by the film sample or the scattered light scattered by the defect on the film sample. An output signal from the light receivers upon receiving the main output beam is also used in the abnormality detection. Even when no defect is present on the film sample, it is likely that presence of a defect is detected erroneously according to the output signal from the light receivers upon receiving the main output beam. Precision in the surface inspection is low.

SUMMARY OF THE INVENTION

In view of the foregoing problems, an object of the present invention is to provide a surface inspection apparatus and method in which precision in photoelectrically detecting defects can be high.

In order to achieve the above and other objects and advantages of this invention, a surface inspection apparatus includes a light source for applying a detection beam to a sample of a film form. A light receiver has plural photoelectric cells arranged in a width direction of the sample, for receiving output light transmitted or reflected by the sample. A defect detector detects a defect on the sample according to an output signal output by each of the photoelectric cells. A sensitivity corrector corrects sensitivity of the photoelectric cells.

The sensitivity corrector is constituted by plural sensitivity correctors for correcting sensitivity of respectively one of the photoelectric cells corresponding thereto, to keep a signal difference of the output signal between the photoelectric cells as small as a predetermined value or less.

The sample is elongated, and the defect is detected while the sample travels continuously.

The photoelectric cells in the light receivers are arranged in a longitudinal direction of the sample in addition to the width direction and positioned in a matrix form.

The photoelectric cells are photomultiplier tubes.

The sensitivity corrector corrects the sensitivity characteristic according to correction information, and the correction information is so determined as to decrease the set sensitivity for one of the photoelectric cells of which said sensitivity characteristic is high, or to increase the set sensitivity for one of the photoelectric cells of which said sensitivity characteristic is low.

Furthermore, plural light valves are disposed on a reception side of the light receiver in association with respectively the photoelectric cells. The correction information is voltage applied to respectively the light valves, to set transmittance thereof.

Preferably, the sensitivity corrector includes plural filters disposed on a reception side of the light receiver in association with respectively the photoelectric cells, for transmitting light. The correction information is transmittance of the filters.

Preferably, the sensitivity corrector includes an amplifier for amplifying the output signal output by each of the photoelectric cells. The correction information is a gain of the amplifier.

The predetermined value is equal to or less than 15%.

Preferably, the predetermined value is equal to or less than 5%.

The light receiver is constituted by a plurality of light receivers arranged on an arcuate curved line defined about a point where the detection beam is incident on the sample.

The plural light receivers are arranged in a zigzag form with reference to the arcuate curved line.

The light source includes a light source device for generating detection light. An optical system condenses the detection light to create a detection beam of a spot shape. A beam scanning device directs the detection beam in the width direction of the sample for scanning.

Preferably, the light source includes a light source device for generating detection light. An optical system condenses the detection light to create a detection beam of a linear shape extending in the width direction of the sample.

In one preferred embodiment, the light source includes a light source device for generating the detection beam. A beam scanning device directs the detection beam in the width direction of the sample for scanning. The sensitivity corrector adjusts the sensitivity of the photoelectric cells in synchronism with scanning of the detection beam.

The sensitivity corrector includes a masking processor, supplied with an output signal output by respectively the photoelectric cells, for eliminating an output signal of a first photoelectric cell among the photoelectric cells from detection processing in the defect detector, the first photoelectric cell being disposed to receive entry of a main output beam obtained by normally transmitting or reflecting the detection beam on the sample.

The masking processor includes a cell determination unit for determining a location of the first photoelectric cell among the photoelectric cells according to start time of scanning of the detection beam with the beam scanning device. A switching device turns on and off an output of the output signal from the first photoelectric cell to the defect detector.

Also, a surface inspection apparatus includes a light source for applying a detection beam to a sample of a film form. A light receiver has plural photoelectric cells arranged in a width direction of the sample, for receiving output light transmitted or reflected by the sample. A defect detector detects a defect on the sample according to an output signal output by each of the photoelectric cells. A sensitivity corrector reduces a sensitivity difference between the photoelectric cells to a predetermined value or less.

Also, a surface inspection apparatus includes a light source for applying a detection beam to a sample of a film form. A beam scanning device directs the detection beam in a width direction of the sample for scanning. A light receiver has plural photoelectric cells arranged in the width direction of the sample, for receiving output light transmitted or reflected by the sample. A masking processor is supplied with an output signal output by respectively the photoelectric cells, for eliminating an output signal of a first photoelectric cell among the photoelectric cells from detection processing, the first photoelectric cell being disposed to receive entry of a main output beam obtained by normally transmitting or reflecting the detection beam on the sample. A defect detector detects a defect on the sample according to the output signal output by each of the photoelectric cells.

Also, a surface inspection apparatus includes a light source for applying a detection beam to a sample of a film form. A beam scanning device directs the detection beam in a width direction of the sample for scanning. A light receiver has plural photoelectric cells arranged in the width direction of the sample, for receiving output light transmitted or reflected by the sample. A sensitivity controller sets sensitivity of the photoelectric cells in synchronism with scanning of the detection beam. A defect detector detects a defect on the sample according to an output signal output by each of the photoelectric cells.

Also, a surface inspection method includes a step of applying a detection beam to a sample of a film form. A sensitivity difference between photoelectric cells is reduced to a predetermined value or less, the photoelectric cells being arranged in a width direction of the sample, for receiving output light transmitted or reflected by the sample. A defect is detected on the sample according to an output signal output by each of the photoelectric cells.

Also, a surface inspection method includes a step of applying a detection beam to a sample of a film form. The detection beam is directed in a width direction of the sample for scanning. Photoelectric cells are selectively switched on and off in synchronism with scanning of the detection beam, the photoelectric cells being arranged in the width direction of the sample, for receiving output light transmitted or reflected by the sample. A defect is detected on the sample according to an output signal output by one of the photoelectric cells being switched on.

Also, a surface inspection method includes a step of applying a detection beam to a sample of a film form. The detection beam is directed in a width direction of the sample for scanning. Sensitivity of photoelectric cells is set in synchronism with scanning of the detection beam, the photoelectric cells being arranged in the width direction of the sample, for receiving output light transmitted or reflected by the sample. A defect is detected on the sample according to an output signal output by each of the photoelectric cells.

Accordingly, precision in photoelectrically detecting defects can be high, because an output noise component included in an output of the light receiver can be lowered by control of sensitivity of the photoelectric cells.

BRIEF DESCRIPTION OF THE DRAWINGS

The above objects and advantages of the present invention will become more apparent from the following detailed description when read in connection with the accompanying drawings, in which:

FIG. 4 is an explanatory view illustrating sensitivity of photomultiplier tubes;

FIGS. 6A-6H are explanatory views illustrating one-dimensional distribution images of scattered light detected by the photomultiplier tubes;

DETAILED DESCRIPTION OF THE PREFERRED EMBODIMENT(S) OF THE PRESENT INVENTION

Figure 1:
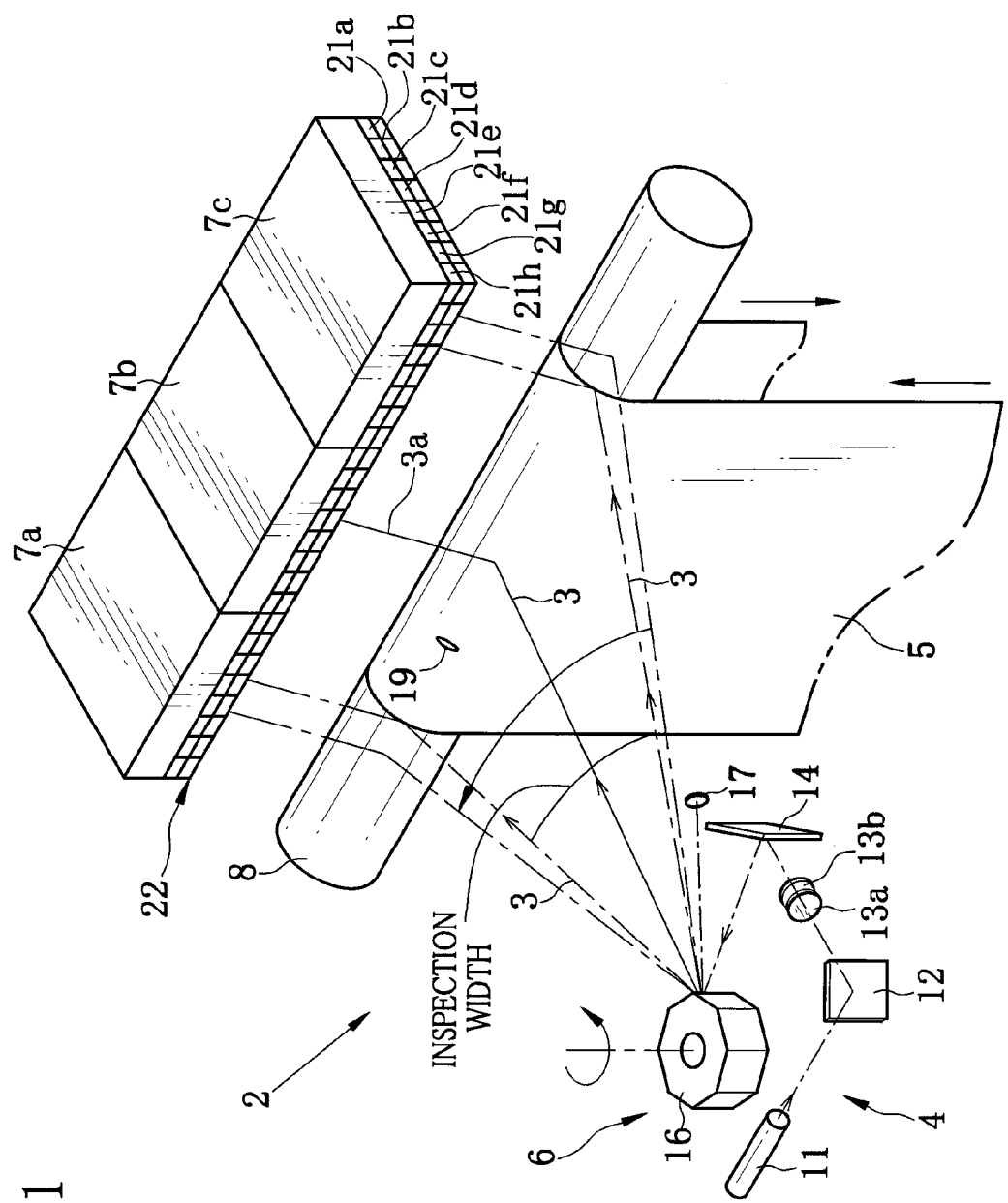
FIG. 1 is a perspective view illustrating a surface inspection apparatus.

A first preferred embodiment of a surface inspection apparatus 2 in FIG. 1 is described. The surface inspection apparatus 2 includes a laser light source 4, a beam scanning device 6, and light receivers 7a, 7b and 7c. A detection laser beam 3 is emitted by the laser light source 4. There is a film sample 5 which the beam scanning device 6 scans in its width direction by directing the detection laser beam 3 suitably. The light receivers 7a-7c or sensor arrays receive the beam reflected by the film sample 5. A support roller 8 is disposed to contact the film sample 5 for transport in a longitudinal direction.

The laser light source 4 includes a laser oscillator 11, a mirror 12 or reflector, lenses 13a and 13b in an optical system, and a mirror 14 or reflector. A laser beam output by the laser oscillator 11 is reflected by the mirror 12, becomes incident upon the lenses 13a and 13b, where the detection laser beam 3 is emitted with a predetermined diameter, for example, 0.33 mm as viewed on a surface of the film sample 5. The detection laser beam 3 from the lens 13b is reflected by the mirror 14 and becomes incident on the beam scanning device 6.

The beam scanning device 6 includes a polygon mirror 16 and a reference sensor 17. The polygon mirror 16 rotates in a counterclockwise direction at a high speed, and reflects the detection laser beam 3 from the mirror 14 for scanning in the width direction of the film sample 5. The reference sensor 17 receives the detection laser beam 3 at a point shortly before scanning of the film sample 5, and outputs a passage signal for reference in scan setting.

Figure 2A:
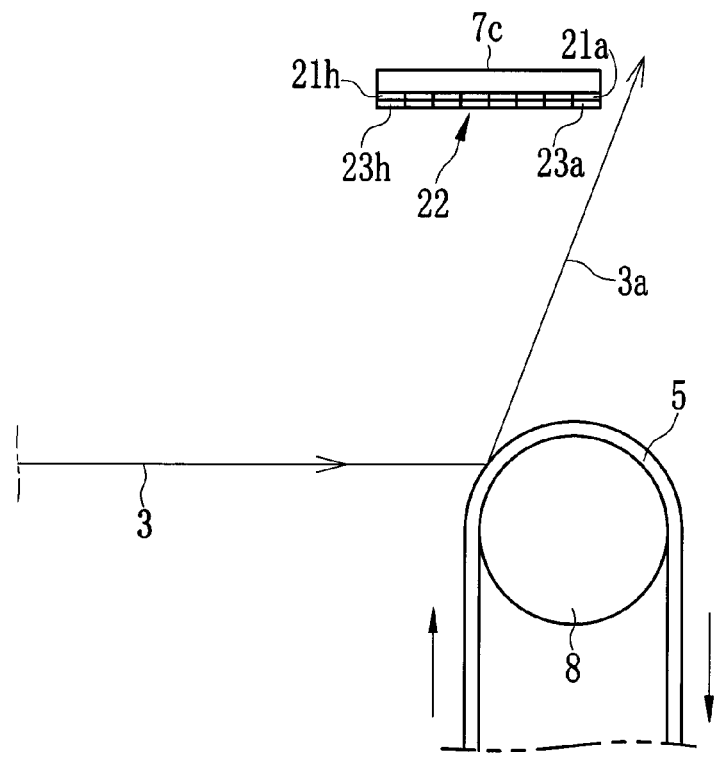
FIGS. 2A and 2B are side elevations illustrating a film sample and light receivers.
Figure 2B:
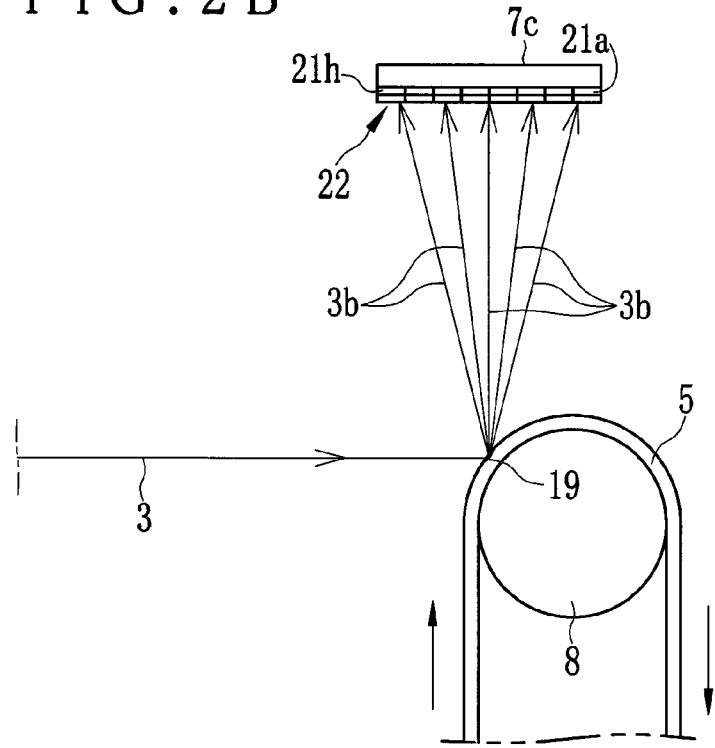
Figure 3:
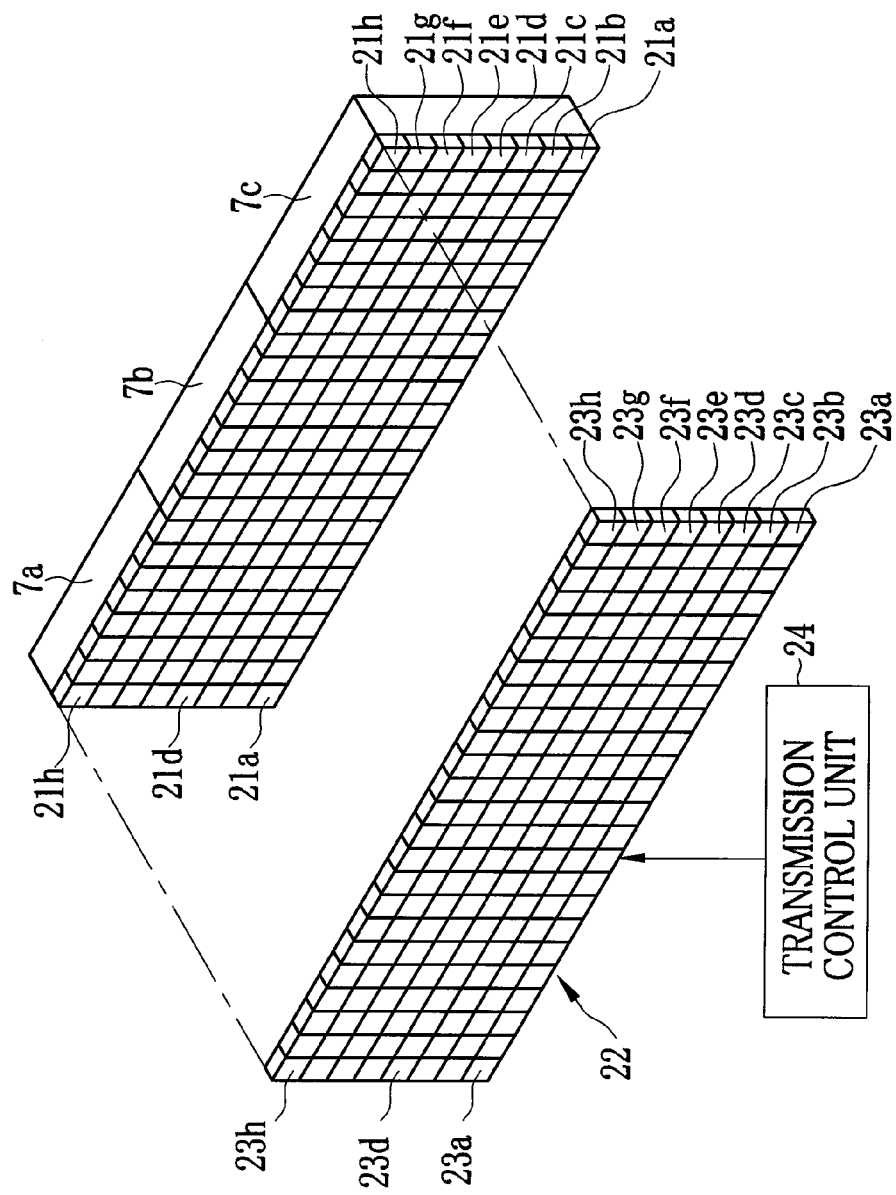
FIG. 3 is a perspective view illustrating the light receivers and a liquid crystal display panel.

In FIGS. 1-3, the light receivers 7a-7c are disposed higher than the support roller 8. A normally reflected laser beam 3a is obtained by normal reflection of the detection laser beam 3 on the film sample 5 at a smooth portion without a defect. See FIG. 2A. If a defect 19 of the film sample 5 receives the detection laser beam 3, scattered light 3b is obtained by scatter at the defect 19. See FIG. 2B. The light receivers 7a-7c are so arranged as to receive the scattered light 3b without receiving the normally reflected laser beam 3a.

Each of the light receivers 7a-7c is a multiple photomultiplier. 64 photomultiplier tubes 21 or photoelectric cells or light sensing elements constitute each multiple photomultiplier in a manner of eight arrays each of which includes eight of the photomultiplier tubes 21. Directions of a two-dimensional form of the photomultiplier tubes 21 are a width direction and a longitudinal direction of the film sample 5. The light receivers 7a-7c are arranged in a single unit. In one array, 24 of the photomultiplier tubes 21 are arranged. First to eighth arrays of photomultiplier tubes 21a-21h are arranged in the forward direction. The light receivers 7a-7c are constituted by Hamamatsu H8500 flat panel PMTS (trade name) of 8×8 cells produced by Hamamatsu Photonics Co, Ltd. Note that the number of the photomultiplier tubes 21 is modifiable suitably for the purpose. In use of the Hamamatsu H8500 flat panel PMTS, a clearance between the photomultiplier tubes 21 in the light receivers 7a-7c is approximately 0.2 mm. A clearance between the light receivers 7a-7c is approximately 3 mm.

The light receivers 7a-7c are disposed for incidence of the scattered light 3b scattered in an angular range of 75-105 degrees relative to a direction of the detection laser beam 3. Specifically, the photomultiplier tubes 21a receive the scattered light 3b scattered in an angular range of 75-78.75 degrees. The photomultiplier tubes 21b receive the scattered light 3b scattered in an angular range of 78.75-82.5 degrees. Also, the photomultiplier tubes 21c-21h receive the scattered light 3b scattered in an angular range of a size of 3.75 degrees. The photomultiplier tubes 21h receive the scattered light 3b scattered in an angular range of 101.25-105 degrees. The photomultiplier tubes 21a-21h create an output signal (sensor output signal) including intensity information according to intensity of the scattered light 3b.

A liquid crystal display panel 22 is attached to a receiving surface of the light receivers 7a-7c directed downwards in FIGS. 1 and 2. 192 light valves 23 constitute the liquid crystal display panel 22, and are arranged in eight arrays respectively including 24 elements in correspondence with the photomultiplier tubes 21a-21h. Specifically, first to eighth light valve arrays 23a-23h by way of a sensitivity corrector are included in the liquid crystal display panel 22. A transmission control unit 24 or sensitivity corrector is connected to the light valve arrays 23a-23h.

In the light receivers 7a-7c, the photomultiplier tubes 21 are tightly positioned in the form of the plural arrays. Voltage for application to the photomultiplier tubes 21a-21h is common. It is likely that a sensitivity difference is created in a sensitivity characteristic of light in the photomultiplier tubes 21a-21h. See numerical values in FIG. 4. The sensitivity is a ratio relative to 100 for a highest sensitivity, and is dimensionless. The sensitivity is higher according to highness of its numerical value, and is lower according to lowness of its numerical value. In the photomultiplier tubes 21g, the second, 10th and 18th have a highest sensitivity characteristic as viewed in the rightward direction. In the photomultiplier tubes 21b, the eighth, 16th and 24th have a lowest sensitivity characteristic as viewed in the rightward direction.

Should there be a sensitivity difference between the photomultiplier tubes 21a-21h, differences occur in the intensity information at the photomultiplier tubes 21a-21h upon receiving the scattered light 3b even of an equal light amount. To prevent such a problem, the transmission control unit 24 controls voltage to be applied to the light valve arrays 23a-23h discretely to change the optical transmittance of the light valve arrays 23a-23h, so that the sensitivity difference in the set sensitivity of the photomultiplier tubes 21a-21h relative to the scattered light 3b is set equal to or less than a reference level, for example 5%. Specifically, upon incidence of the scattered light 3b of an equal light amount, equal intensity information of scattered light is obtained at any one of the photomultiplier tubes 21a-21h. Note that a sensitivity difference (%) is defined as $[(S1-S2)/S1] \times 100$ where S1 is a highest level of a set sensitivity after correction with the light valves 23, and S2 is a lowest level of the set sensitivity after the correction. Should the sensitivity difference be more than 15%, the precision of detecting defects will be considerably low. Accordingly, a sensitivity difference is preferably equal to or less than 15%, and desirably equal to or less than 5%.

In the transmission control unit 24, the transmittance of one of the light valves 23 corresponding to one of the photomultiplier tubes 21 having a lowest sensitivity characteristic is set at 100%. The transmission control unit 24 determines the transmittance of remaining ones of the light valve arrays 23a-23h according to this. A set is defined as a combination of the one of the photomultiplier tubes 21 having the lowest sensitivity characteristic and its corresponding one of the light valves 23. The set sensitivity of the set for abnormality detection is determined from [the sensitivity characteristic of the photomultiplier tube 21]×[the transmittance of the light valve 23]. The set sensitivity is $50 \times 100(\%) = 5,000(\%)$. Also, the transmission control unit 24 controls to determine the set sensitivity of the remainder of the light valves 23 with the remainder of the photomultiplier tubes 21 at 5,000.

For example, the highest sensitivity characteristic of one of the photomultiplier tubes 21 is 100. Transmittance of one of the light valves 23 corresponding to this is set at 50% in order to determine the set sensitivity at 5,000. Transmittance of one of the light valves 23 corresponding to one of the photomultiplier tubes 21 having the sensitivity of 79 (fifth of the photomultiplier tubes 21$h$ as viewed in the rightward direction in the eighth array) is 63.3%. Similarly, the sensitivity of a corresponding one of the light valves 23 is controlled to determine the set sensitivity of the remainder of the photomultiplier tubes 21 commonly as high as 5,000. This control is effective in reducing the sensitivity difference to 5% or less for safely detecting defects.

It is preferable periodically to measure sensitivity characteristics of the photomultiplier tubes 21$a$-21$h$ to control transmittance of the light valve arrays 23$a$-23$h$ according to the measured sensitivity characteristics. Even when the sensitivity characteristics of the photomultiplier tubes 21$a$-21$h$ are changed with time, it is unnecessary to renew the photomultiplier tubes 21$a$-21$h$, because only the transmittance of the light valve arrays 23$a$-23$h$ can be changed.

Figure 5:
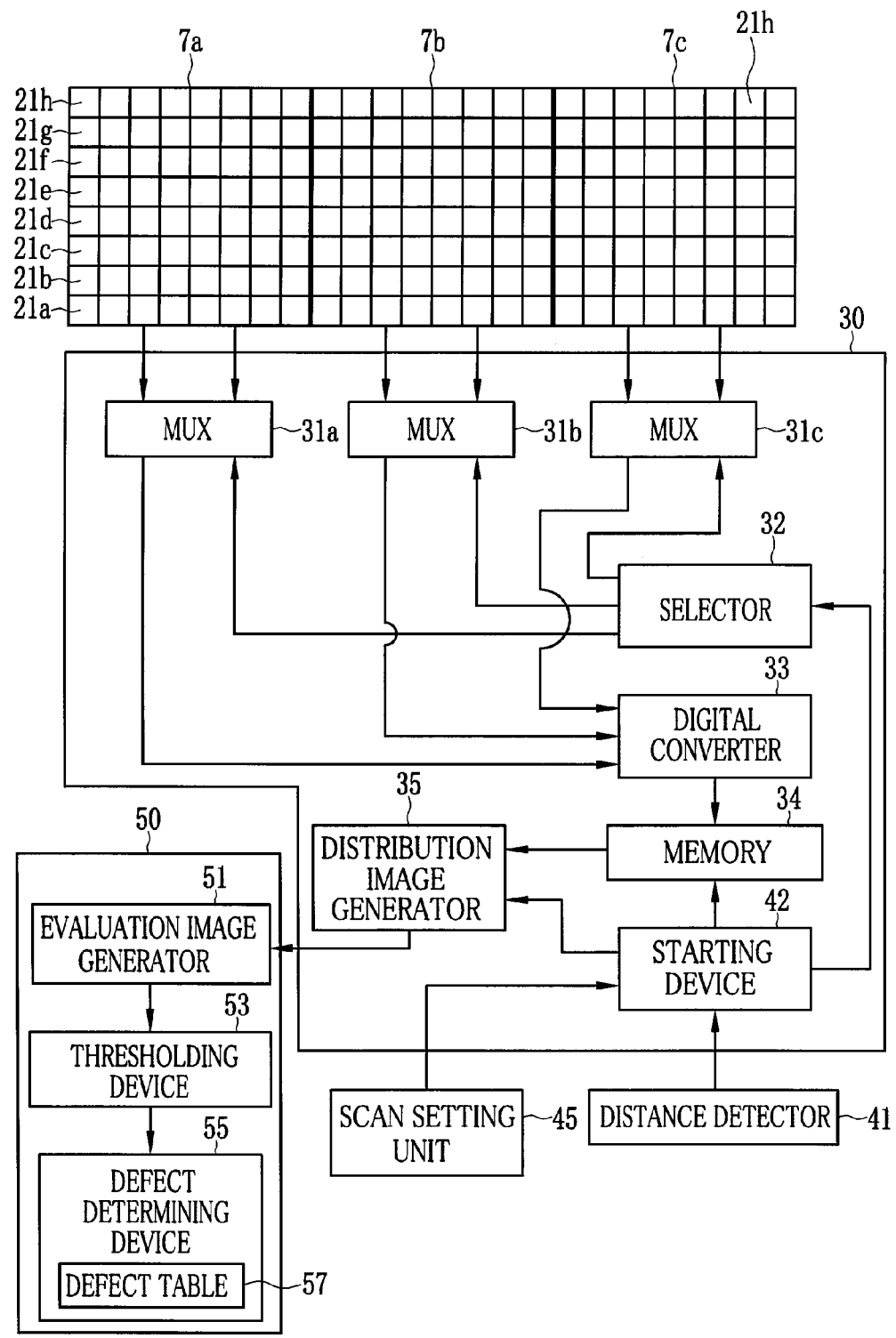
FIG. 5 is a block diagram schematically illustrating circuit elements in the surface inspection apparatus.

In FIG. 5, an intensity distribution determiner 30 is connected to the photomultiplier tubes 21$a$-21$h$ of the light receivers 7$a$-7$c$. Multiplexers 31$a$, 31$b$ and 31$c$ in the intensity distribution determiner 30 select particular ones of the photomultiplier tubes 21$a$-21$h$ for acquiring an output signal being created. A selector 32 for selection control generates a command signal. According to the command signal, the multiplexers 31$a$-31$c$ select one of the photomultiplier tubes 21 for acquiring the output signal. In the embodiment, the multiplexers 31$a$-31$c$ select the photomultiplier tubes 21$a$ one after another in the first array from the left end to the right end, and select the photomultiplier tubes 21$b$ one after another in the second array from the left end to the right end, and select the photomultiplier tubes 21$c$-21$h$ one after another in each of the third to eighth arrays from the left end to the right end.

A digital converter 33 converts intensity information of an output signal generated in the multiplexers 31$a$-31$c$ into intensity data as digital data of the scattered light. Also, the digital converter 33 adds location data (cell position) to the intensity data for a location of any of the photomultiplier tubes 21$a$-21$h$. A memory 34 is used, in which the intensity data is written.

A distribution image generator 35 reads the intensity data from the memory 34. In FIGS. 6A-6H, distribution curves 37$a$-37$h$ or one-dimensional distribution images for scattered light are created for the photomultiplier tubes 21$a$-21$h$.

A distance detector 41 determines a moving speed of the film sample 5 according to diameter data and rotational speed of the support roller 8. A moving distance of the film sample 5 is detected according to the moving speed and the driving time. The distance detector 41 outputs a start signal for abnormality detection at each time that the moving distance reaches a predetermined reference distance. A starting device 42 for timing control is supplied with the start signal. Note that the moving distance may be detected according to the diameter data and rotational speed of the support roller 8.

There is a scan setting unit 45 to which a passage signal is input. The scan setting unit 45 operates according to data including predetermined width data of an inspection width depending on a width of the film sample 5, a scan speed of the detection laser beam 3, and elapsed time from a time point of the input of the passage signal, and checks whether the detection laser beam 3 is emitted in the inspection width. According to a result of the detection, it is determined whether an in-place signal should be supplied to the starting device 42 or not.

The starting device 42 checks whether the in-place signal is input from the scan setting unit 45, outputs a start signal to the selector 32 and the distribution image generator 35 and determines whether the selector 32 and the distribution image generator 35 should be driven.

To a defect detector 50, information of the distribution curves 37$a$-37$h$ from the distribution image generator 35 is input. An evaluation image generator 51 in the defect detector 50 combines the distribution curves 37$a$-37$h$ in FIG. 7 for image synthesis, so that an evaluation image 52 is created in a two-dimensional form with a coordinate in the film width direction and a coordinate of a scattering angle. A thresholding device 53 for extraction binarizes the evaluation image 52 to determine a defect area 52$a$ and a normal area 52$b$. The defect area 52$a$ is hatched in FIG. 7, where intensity in the evaluation image 52 is higher than a threshold. In the normal area 52$b$, intensity in the evaluation image 52 is lower than the threshold. The thresholding device 53 extracts highest intensity information in the defect area 52$a$ of each of unit ranges of angles, for example 3.75 degrees from 75 degrees, and extracts a defect size of the defect area 52$a$ in the film width direction. A defect determining device 55 is supplied with information of the highest intensity information and the defect size.

A defect table 57 is stored in the defect determining device 55, and is constituted by plural reference defect data, each of which is a combination of highest intensity information of a defect area, a length of a defect in the film width direction, and other specific information. The defect determining device 55 compares the defect data in the defect table 57 with specific information from the thresholding device 53 including the highest intensity information of the defect area 52$a$ of the respective angular regions and the defect size in the film width direction. The defect determining device 55 retrieves defect data identical with or near to the input specific information among a plurality of the stored defect data, so as to determine a type, size and location of defects present on the film sample 5.

The operation of the embodiment is described now. To inspect a surface of the film sample 5 for defects, at first the detection laser beam 3 is emitted by the laser light source 4. The detection laser beam 3 becomes incident upon the beam scanning device 6.

The beam scanning device 6 directs the detection laser beam 3 by use of the polygon mirror 16 in rotation for scanning in the width direction of the film sample 5. The reference sensor 17 receives the detection laser beam 3 at a point shortly before scanning of the film sample 5 with the detection laser beam 3, and outputs a passage signal to the scan setting unit 45.

If no defect is present on the film sample 5 in FIG. 2A, the detection laser beam 3 is totally reflected by the film sample 5 to become the normally reflected laser beam 3$a$, which does not become incident upon the light receivers 7$a$-7$c$. No output signal is input to the digital converter 33. The defect determining device 55 is not supplied with highest intensity information of a defect, or its defect size in the film width direction.

In FIG. 2B, if the defect 19 is present on the film sample 5, the detection laser beam 3 becomes the scattered light 3$b$ upon scattering on the defect 19 in the course of scanning. The scattered light 3$b$ is received by the photomultiplier tubes 21$a$-21$h$ of the light receivers 7$a$-7$c$. The photomultiplier tubes 21a-21h create an output signal including the intensity information of the scattered light 3b.

The light valve arrays 23a-23h are controlled for their optical transmittance by control of their voltage applied by the transmission control unit 24. A sensitivity difference between the photomultiplier tubes 21a-21h in response to the scattered light 3b is set equal to or less than 5%. Output noise suppression can be carried out by minimizing the sensitivity difference between the photomultiplier tubes 21a-21h. Therefore, precision in detecting defects can be prevented from dropping.

The distance detector 41 detects a moving distance of the film sample 5, and outputs a start signal to the starting device 42 at each time of reach of the moving distance to the reference distance.

The scan setting unit 45 checks whether the detection laser beam 3 is output in the inspection width. If the scan setting unit 45 judges that the detection laser beam 3 is emitted in the inspection width, the scan setting unit 45 outputs an in-place signal to the starting device 42. If the scan setting unit 45 judges that the detection laser beam 3 is not emitted in the inspection width, the scan setting unit 45 stops outputting an in-place signal to the starting device 42.

While the in-place signal is input, the starting device 42 outputs the start signal to the selector 32 and the distribution image generator 35. While no in-place signal is input, the starting device 42 does not output a start signal to the selector 32 or the distribution image generator 35.

While the start signal is input, the selector 32 causes the multiplexers 31a-31c to operate. In the multiplexers 31a-31c, the photomultiplier tubes 21a-21h in each of the arrays are selected one another from the left end to the right end, to acquire the output signal from the photomultiplier tubes 21a-21h.

The intensity information of the output signal obtained by the multiplexers 31a-31c is converted into intensity data by the digital converter 33. The digital converter 33 adds location data (cell position) to the intensity data for any one of locations of the photomultiplier tubes 21a-21h. The intensity data is written to the memory 34.

While the start signal is input, the distribution image generator 35 reads the intensity data from the memory 34. In FIG. 6, the distribution image generator 35 creates the distribution curves 37a-37h of the photomultiplier tubes 21a-21h.

Figure 7:
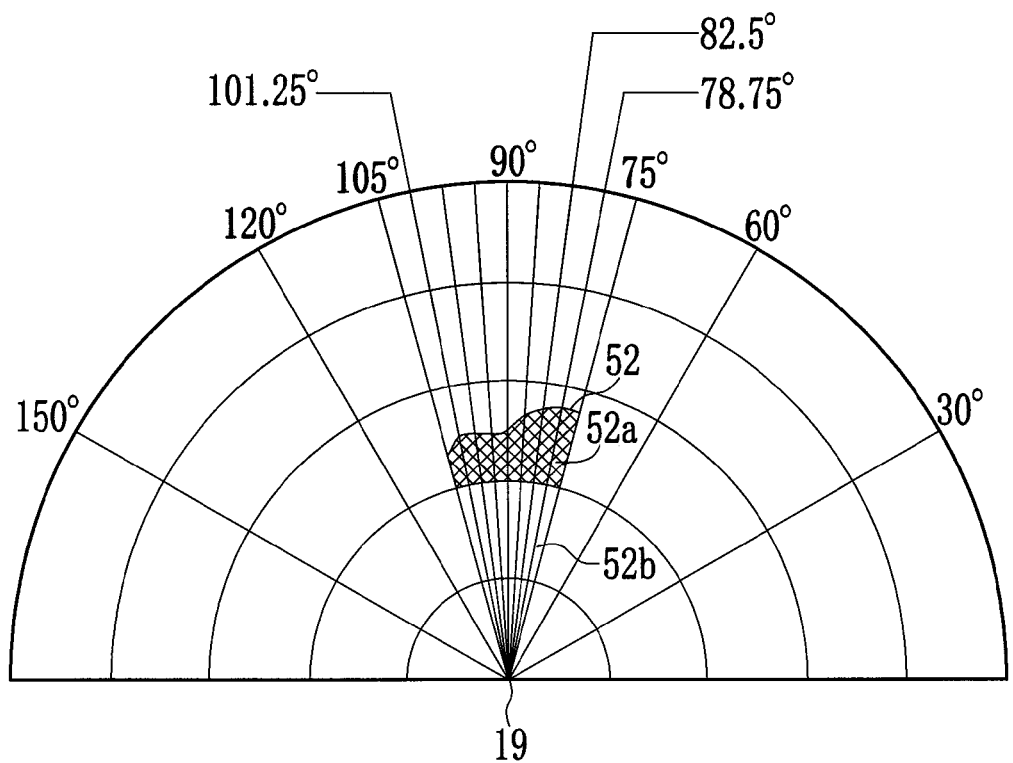
FIG. 7 is an explanatory view illustrating an evaluation image formed by combining the distribution images.

Information of the distribution curves 37a-37h created by the distribution image generator 35 is input to the evaluation image generator 51. In FIG. 7, the evaluation image generator 51 combines the distribution curves 37a-37h to generate the evaluation image 52 in a two-dimensional form with a coordinate in the film width direction and a coordinate of a scattering angle. The thresholding device 53 binarizes the evaluation image 52 to form the defect area 52a in which the intensity is higher than the threshold and the normal area 52b in which the intensity is lower than the threshold. A defect size in the film width direction and the highest intensity information in the defect area 52a in each of the angular ranges are extracted and output to the defect determining device 55.

The defect determining device 55 compares specific information with the defect data stored in the defect table 57, the specific information including the highest intensity information of the defect area 52a of each one of the angular range, and the defect size of the defect area 52a in the film width direction. The defect determining device 55 retrieves defect data identical with or near to the input specific information among a plurality of the stored defect data, so as to determine a type, size and location of defects present on the film sample 5.

A result of detection in the defect determining device 55 and detected defect data are written to the memory 34. It is additionally possible to notify the detection result and the detected defect data by use of a user interface, for example with an image displayed on a display panel, or with sound emitted by a loudspeaker.

In FIGS. 8, 9, 10 and 11, a second preferred surface inspection apparatus 60 is illustrated, and includes first light receivers 61a, 61b and 61c, second light receivers 62a, 62b and 62c, third light receivers 63a, 63b and 63c, fourth light receivers 64a, 64b and 64c and fifth light receivers 65a, 65b and 65c. Among those, the light receivers 61a, 62a, 63a, 64a and 65a are arranged on an arc of a circle defined about a point where the detection laser beam 3 becomes incident upon the film sample 5. Elements similar to those of the above embodiment are designated with identical reference numerals. The laser light source 4 and the beam scanning device 6 are not depicted in FIGS. 8 and 10 for simplification.

Each of the light receivers 61a-65c is sensor arrays constituted by the photomultiplier tubes 21a-21h in a manner similar to the light receivers 7a-7c. The intensity distribution determiners 30 are five corresponding to the light receivers 61a-65c.

The first light receivers 61a-61c are so arranged as to receive entry of the scattered light 3b scattered in an angular range of 15-45 degrees relative to an output direction of the detection laser beam 3. On the photomultiplier tubes 21a of the first array, the scattered light 3b scattered in a range of 15-18.75 degrees becomes incident. On the photomultiplier tubes 21b-21h of the second to eighth arrays, the scattered light 3b scattered in an angular range of 3.75 degrees becomes incident. On the photomultiplier tubes 21h of the eighth array, the scattered light 3b scattered in a range of 41.25-45 degrees becomes incident.

The second light receivers 62a-62c are disposed for receiving the scattered light 3b scattered in an angular range of 45-75 degrees relative to the output direction of the detection laser beam 3. The third light receivers 63a-63c are disposed for receiving the scattered light 3b scattered in an angular range of 75-105 degrees relative to the output direction of the detection laser beam 3. The fourth light receivers 64a-64c are disposed for receiving the scattered light 3b scattered in an angular range of 105-135 degrees relative to the output direction of the detection laser beam 3. The fifth light receivers 65a-65c are disposed for receiving the scattered light 3b scattered in an angular range of 135-165 degrees relative to the output direction of the detection laser beam 3. Refracted light 3d, which is refracted slightly at a defect 68 of the film sample 5, and reflected light 3e reflected at the defect 68 do not become incident upon the light receivers 61a-65c.

Figure 8:
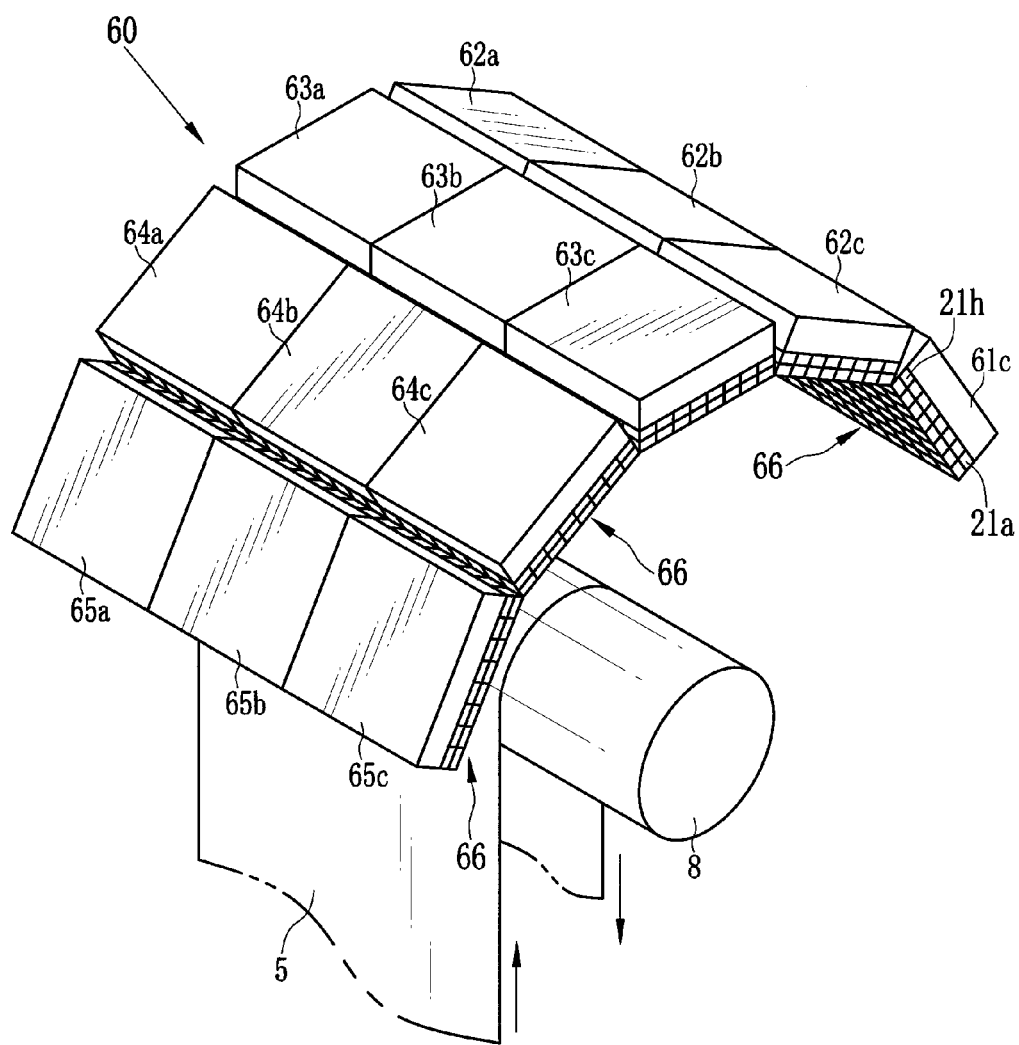
FIG. 8 is a perspective view illustrating one preferred surface inspection apparatus in which light receivers are arranged on an arcuate curved line.
Figure 9:
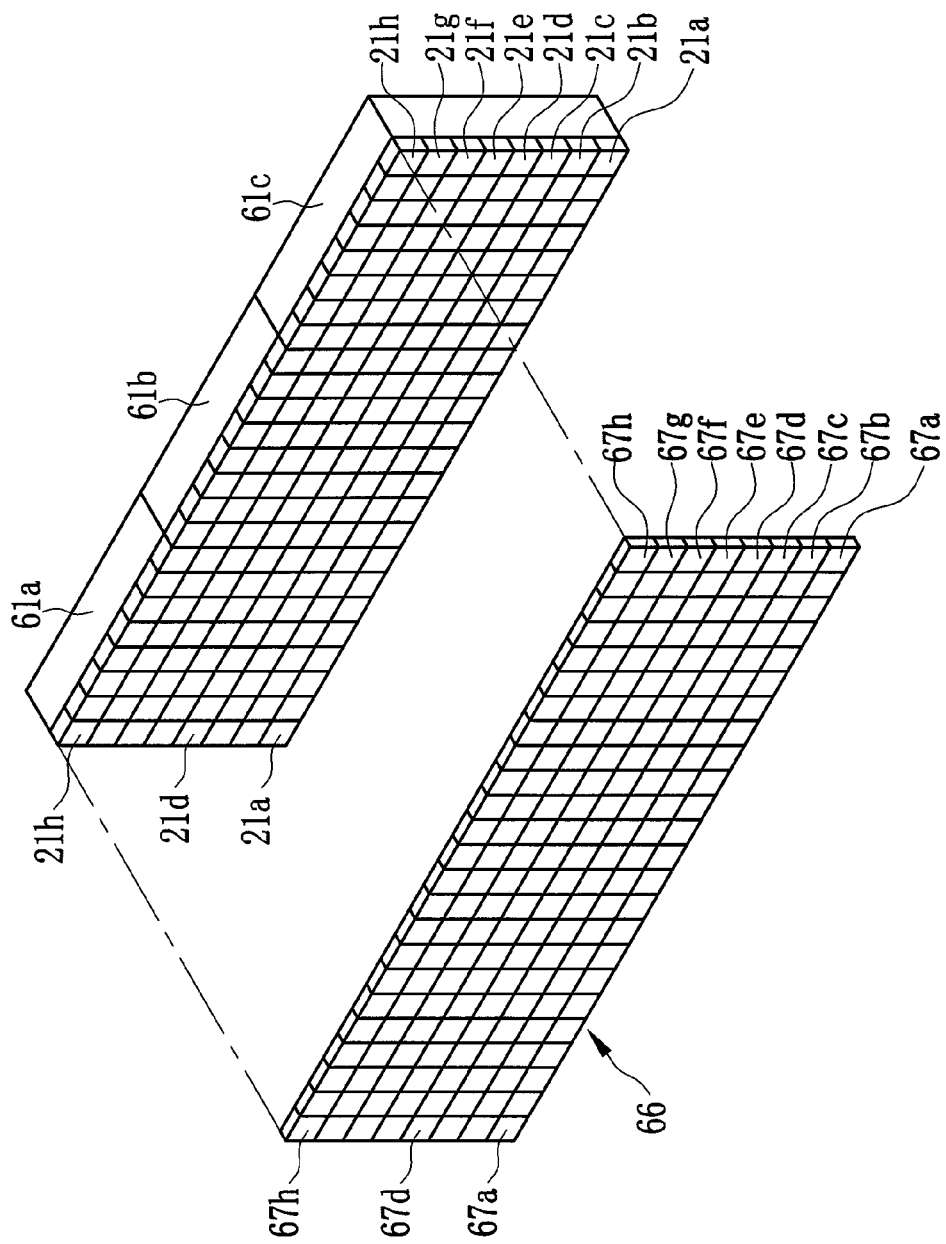
FIG. 9 is a perspective view illustrating the light receivers and a filter unit.
Figure 10:
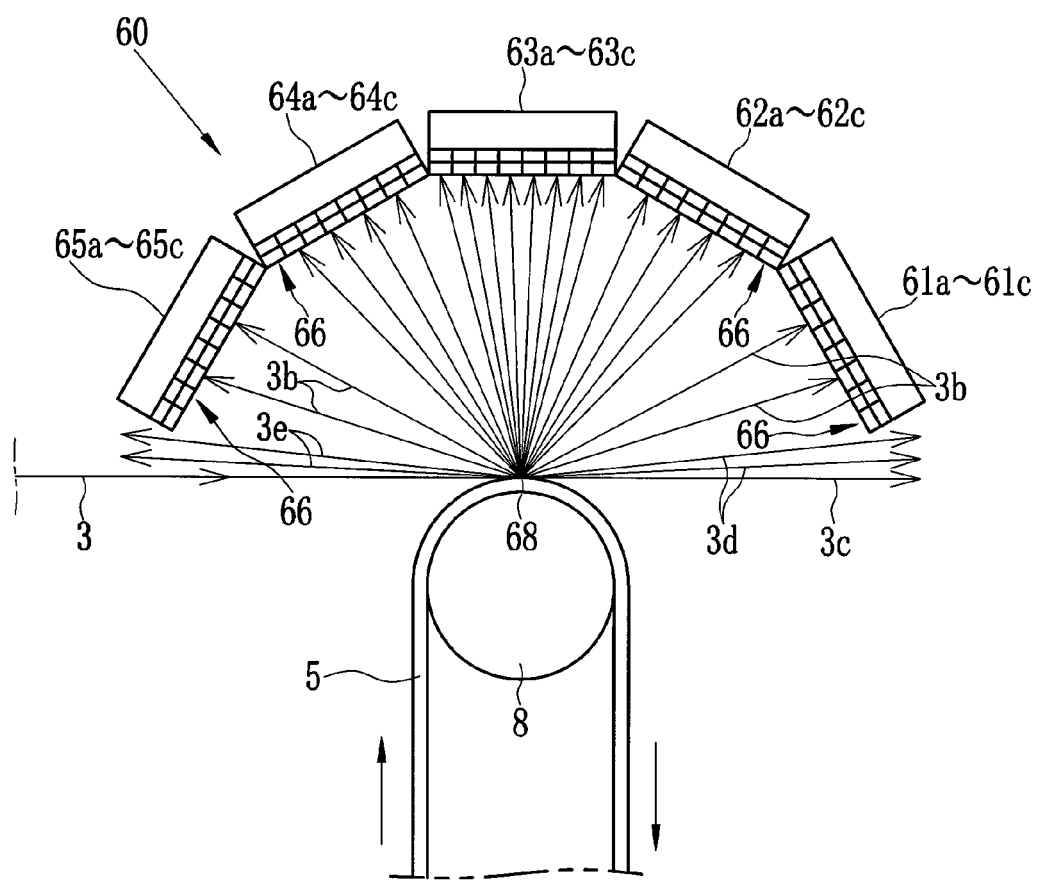
FIG. 10 is a side elevation illustrating the film sample and the light receivers.
Figure 11:
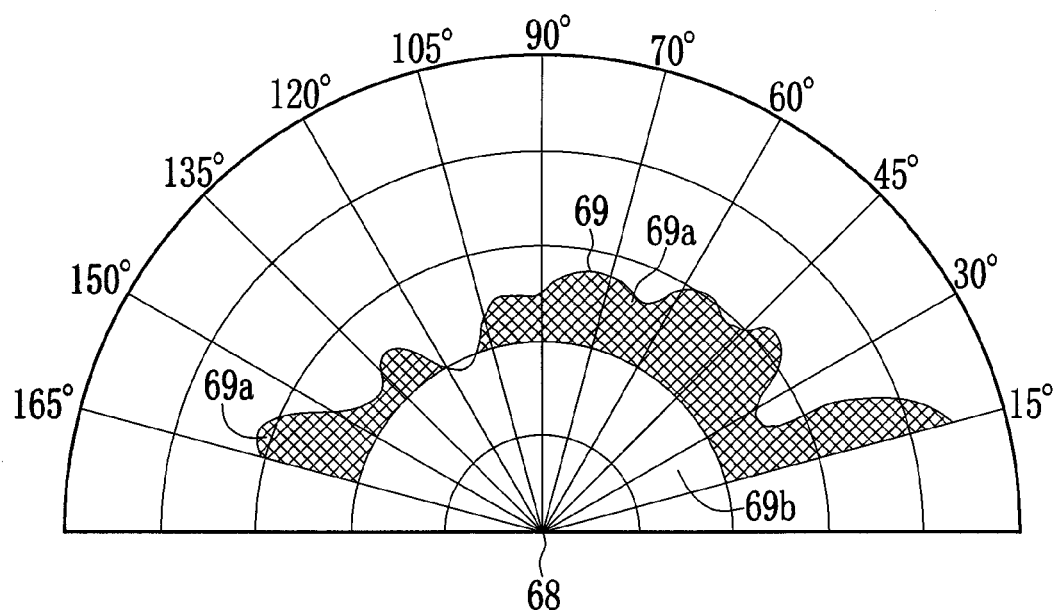
FIG. 11 is an explanatory view illustrating an evaluation image formed by combining distribution images.

A filter unit 66 by way of a sensitivity corrector is attached to a receiving surface of the light receivers 61a-65c directed downwards in FIGS. 8 and 10. 192 ND filters 67 or neutral density filters constitute the filter unit 66, and are arranged in eight arrays respectively including 24 filters in correspondence with the photomultiplier tubes 21a-21h. Specifically, first to eighth filter arrays 67a-67h are included in the filter unit 66.

The filter arrays 67a-67h are constructed for operating in a similar manner to the light valve arrays 23a-23h. The filter arrays 67a-67h have transmittance corresponding to the photomultiplier tubes 21a-21h to reduce a sensitivity difference between the photomultiplier tubes 21a-21h to 5% or less relative to the scattered light 3b. Thus, intensity information of a substantially equal value is obtained upon reception on the photomultiplier tubes 21a-21h in response to the scattered light 3b of an equal light amount. This control is effective in suppressing the sensitivity difference at a low level without a problem.

Note that the filter unit 66 is produced by a suitable method in which sensitivity characteristics of the numerous cells are obtained experimentally for conditioning, and are processed to form a gradation image of a patterned form two-dimensionally. It is possible in the invention to utilize any of various known methods of filter production.

The operation of the embodiment is described. To inspect the surface of the film sample 5 for defects, the detection laser beam 3 is output by the laser light source 4 and scans the film sample 5 in its width direction. Shortly before scanning the film sample 5, the detection laser beam 3 is received by the reference sensor 17, which sends a passage signal to the scan setting unit 45.

If no defect is present on the film sample 5, only a normally transmitted laser beam 3c travels from the film sample 5 after full transmission of the detection laser beam 3. The normally transmitted laser beam 3c does not become incident on the light receivers 7a-7c. No output signal is input to the digital converter 33. No highest intensity information is input to the defect determining device 55. The defect determining device 55 judges a smooth state of the surface of the film sample 5 without a defect if no highest intensity information is input thereto.

If the defect 68 is present on the film sample 5, the detection laser beam 3 is scattered by the defect 68 and becomes the scattered light 3b. The scattered light 3b is received by the photomultiplier tubes 21a-21h of the light receivers 61a-65c. The photomultiplier tubes 21a-21h create an output signal which includes intensity information of intensity of the scattered light 3b being received.

The filter arrays 67a-67h are set at transmittance corresponding to respectively the photomultiplier tubes 21a-21h. A sensitivity difference between the photomultiplier tubes 21a-21h in relation to the scattered light 3b is reduced to 5% or less. This is effective in preventing drop in the precision due to the sensitivity difference between the photomultiplier tubes 21a-21h.

While a start signal is input from the starting device 42, the selector 32 causes the multiplexers 31a-31c to operate. Intensity information of scattered light of the output signal is obtained by the multiplexers 31a-31c, is converted into intensity data by the digital converter 33, and is written to the memory 34.

While a start signal is input from the starting device 42, the distribution image generator 35 reads intensity data from the memory 34, to create the distribution curves 37a-37h of the photomultiplier tubes 21a-21h.

To the evaluation image generator 51, information of the distribution curves 37a-37h from the distribution image generator 35 is input. The evaluation image generator 51 for image synthesis combines the distribution curves 37a-37h for all of the light receivers 61a-65c, so that an evaluation image 69 is created in a two-dimensional form with a coordinate in the film width direction (not shown in FIG. 11) and a coordinate of a scattering angle. The thresholding device 53 for extraction binarizes the evaluation image 69 to determine a defect area 69a and a normal area 69b. The defect area 69a is hatched in FIG. 11. The thresholding device 53 extracts highest intensity information in the defect area 69a of each of unit ranges of angles. The defect determining device 55 is supplied with information of the highest intensity information.

In the same manner as the first embodiment, the defect determining device 55 determines a type, size and location of defects present on the film sample 5.

Consequently, the arcuate arrangement of the light receivers 61a-65c makes it possible reliably to receive the scattered light 3b even upon scatter of the scattered light 3b in a larger area at the defect 68 or even upon its scatter in a limited direction. This is effective in raising precision in the abnormality detection.

In the above embodiments, the light valves or filters control the set sensitivity. In place of this, amplifiers can be used by way of a sensitivity corrector. The output signal output by the photomultiplier tubes can be amplified according to the sensitivity characteristic, to reduce the sensitivity difference between the photomultiplier tubes to 5% or less. For example, an output signal from the photomultiplier tubes 21 having a sensitivity characteristic of 100 can remain without amplification. An output signal from the photomultiplier tubes 21 having a sensitivity characteristic of 50 is amplified by two times. See an amplifier 131 in FIG. 18.

Figure 12:
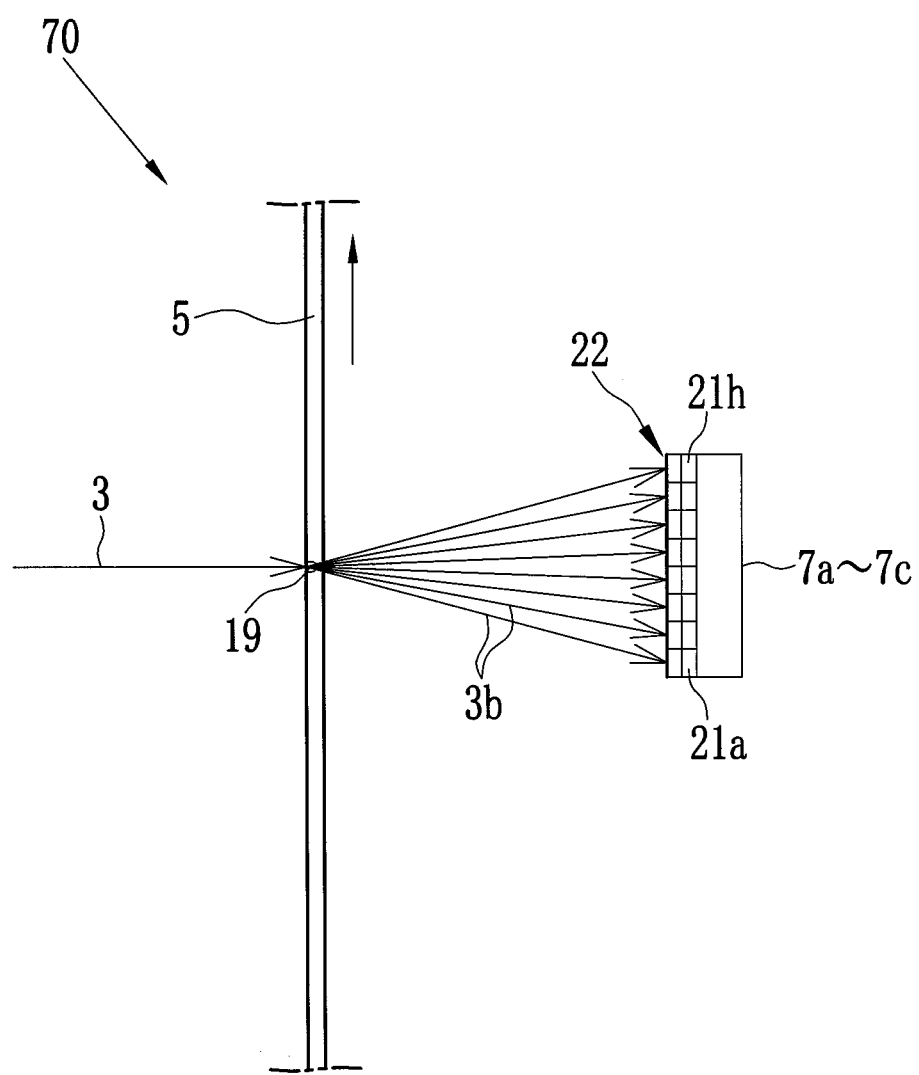
FIG. 12 is a perspective view illustrating another preferred surface inspection apparatus of a transmission type.

In FIG. 12, another preferred surface inspection apparatus 70 is illustrated, in which a light beam transmitted through the film sample 5 is received by the light receivers 7a-7c. A transport mechanism (not shown) moves up the film sample 5, while the detection laser beam 3 is directed to the film sample 5 from the left side. The light receivers 7a-7c are arranged on the right side of the film sample 5, and receive the scattered light 3b scattered at the defect 19 of the film sample 5. In FIG. 12, the laser light source 4 and the beam scanning device 6 are not shown.

Figure 13:
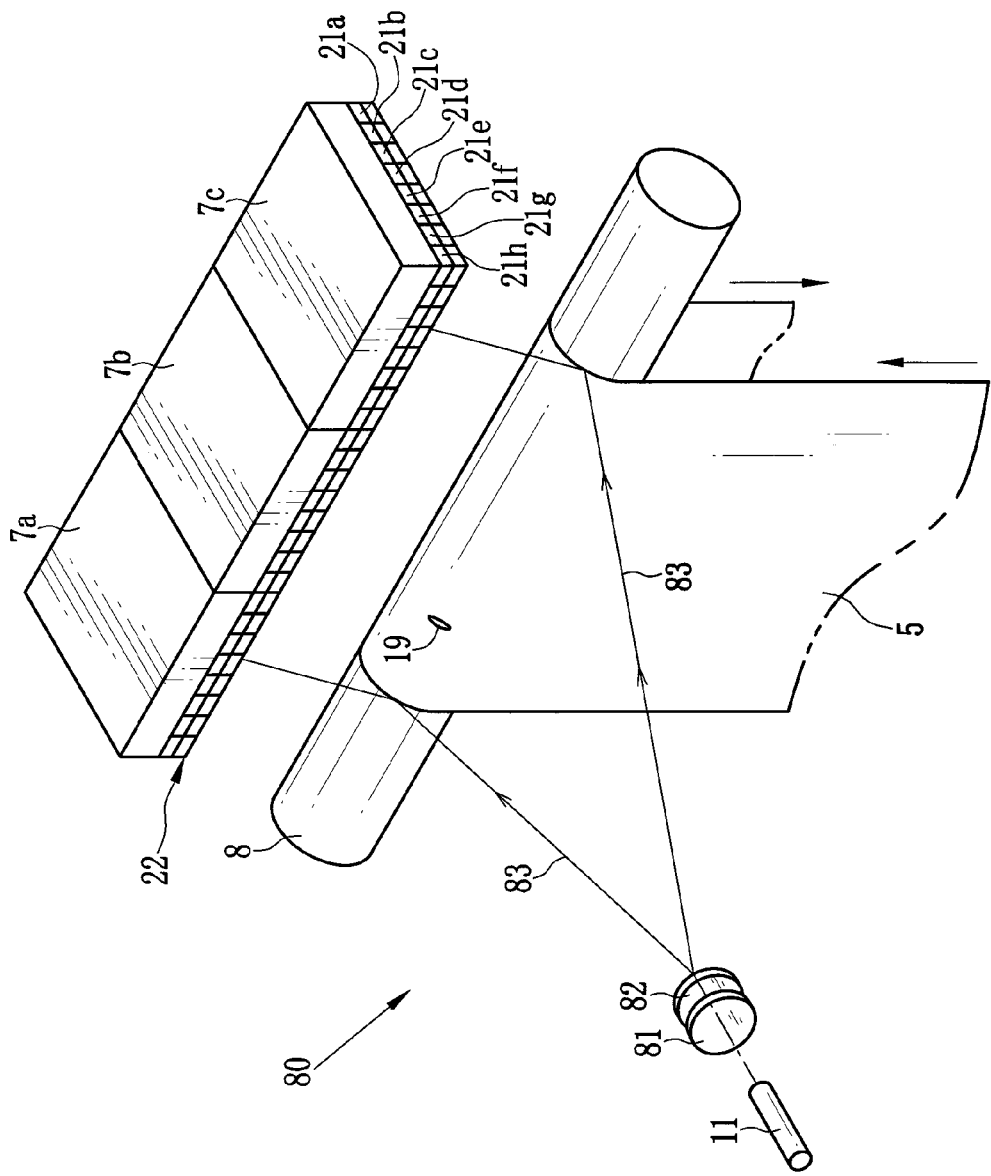
FIG. 13 is a perspective view illustrating one preferred surface inspection apparatus in which a detection beam is in a linear form.

In FIG. 13, still another preferred surface inspection apparatus 80 is illustrated. A first lens 81 in an optical system receives a laser beam from the laser oscillator 11, and enlarges in a film width direction of the film sample 5 (horizontally). A second lens 82 in the optical system is disposed downstream from the first lens 81, and condenses the laser beam from the first lens 81, so that a detection laser beam 83 is obtained in a linear form with a width equal to that of the film sample 5, and applied to the film sample 5.

Figure 14:
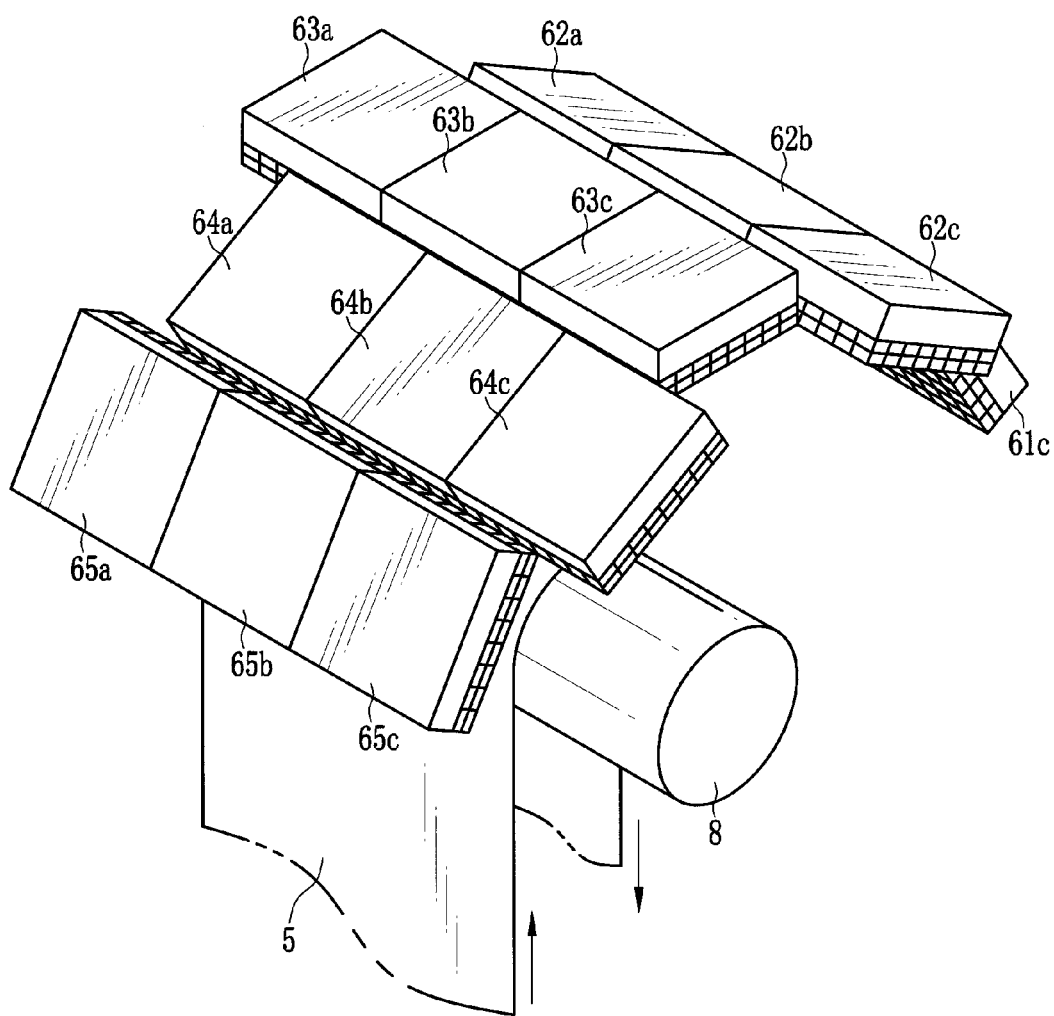
FIG. 14 is a front elevation illustrating light receivers arranged alternately.

In the second preferred embodiment, the right and left ends of the light receivers 61a-65c are aligned. In FIG. 14, another preferred structure is depicted. The right and left ends of the light receivers 61a-65c are offset alternately without alignment, namely are arranged in a zigzag form on an arcuate reference surface.

Figure 15:
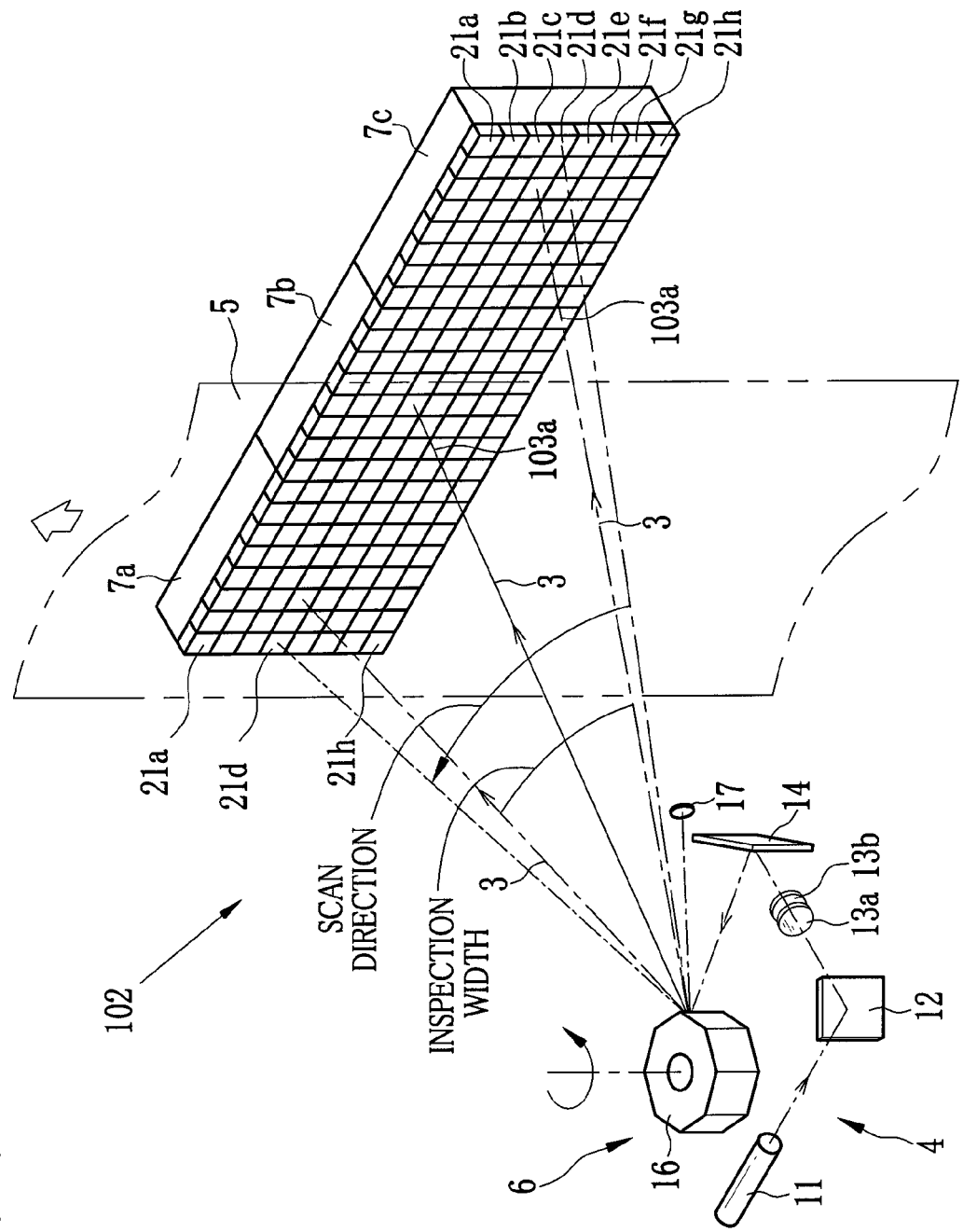
FIG. 15 is a perspective view illustrating another preferred surface inspection apparatus.
Figure 16:
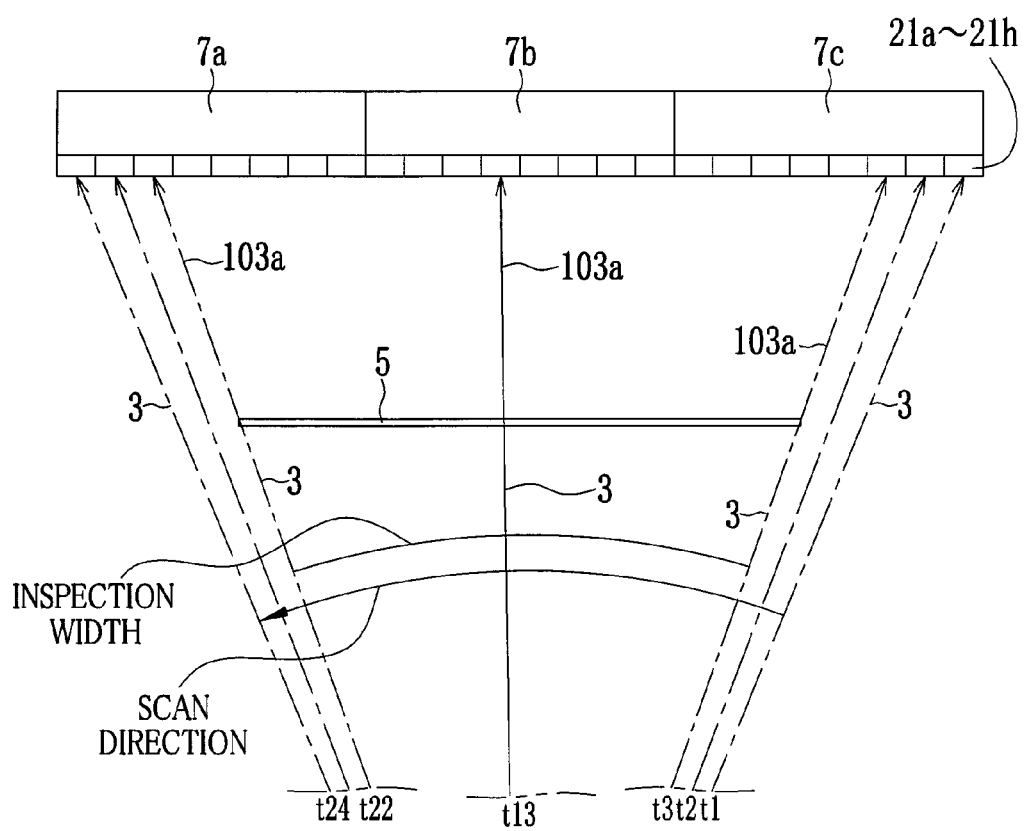
FIG. 16 is a plan illustrating a film sample and light receivers.
Figure 17:
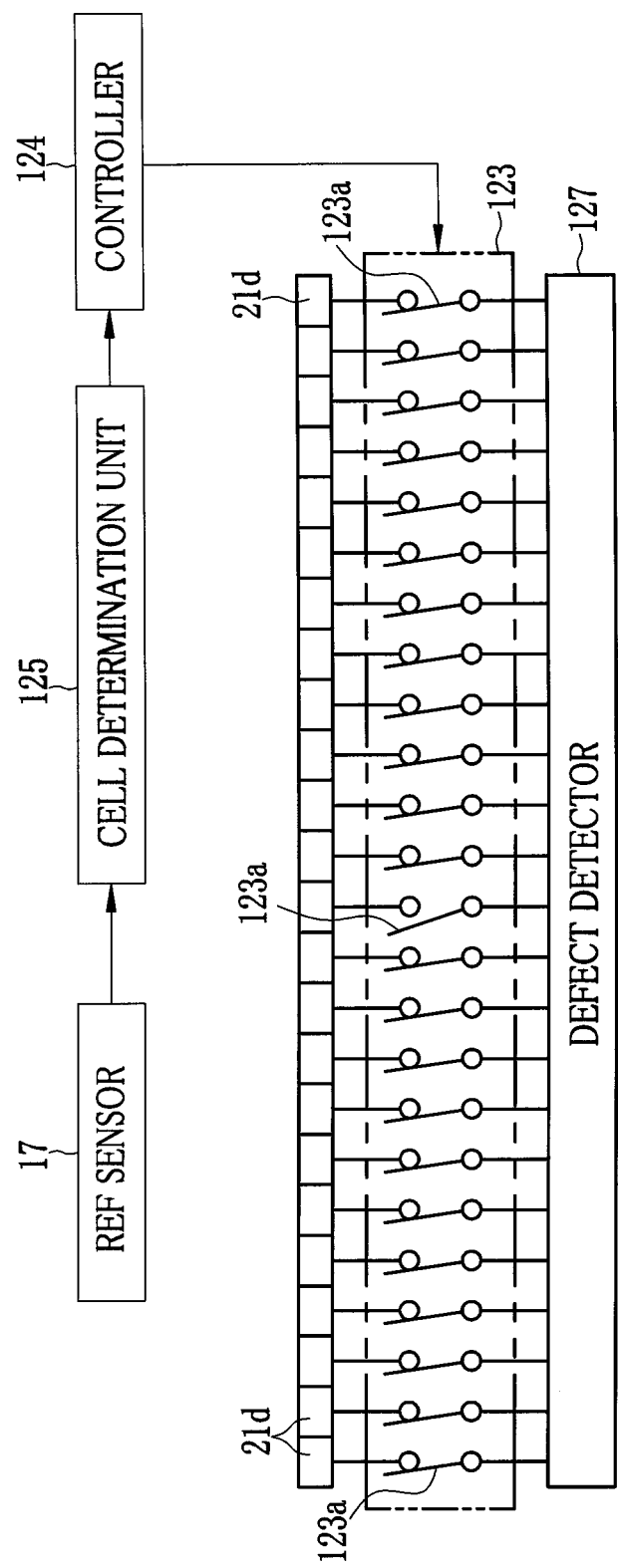
FIG. 17 is a block diagram schematically illustrating circuit elements in the surface inspection apparatus.

In FIGS. 15, 16 and 17, another preferred surface inspection apparatus 102 is illustrated, in which control of electric masking is utilized for output noise suppression.

A normally transmitted laser beam 103a is obtained when a detection laser beam is transmitted through the film sample 5. The photomultiplier tubes 21d as 24 cells in the fourth array are arranged to receive the normally transmitted laser beam 103a. There is a switch array 123 or switching device as masking processor for signal masking, which includes 24 switch elements 123a or switching device connected with the photomultiplier tubes 21d discretely. A controller 124 as sensitivity corrector turns on and off the switch elements 123a discretely.

A cell determination unit 125 for photomultiplier tubes or photoelectric cells or light sensing elements is supplied with a passage signal from the reference sensor 17. The cell determination unit 125 arithmetically determines one of the photomultiplier tubes 21d of entry of the normally transmitted laser beam 103a among the photomultiplier tubes 21d of the fourth array according to a scan speed of the detection laser beam 3 with the polygon mirror 16 and time elapsed from the input of the passage signal.

A defect detector 127 is connected with the switch elements 123a. Not only the photomultiplier tubes 21d but the photomultiplier tubes 21a-21c and 21e-21h are connected with the defect detector 127.

Figure 18:
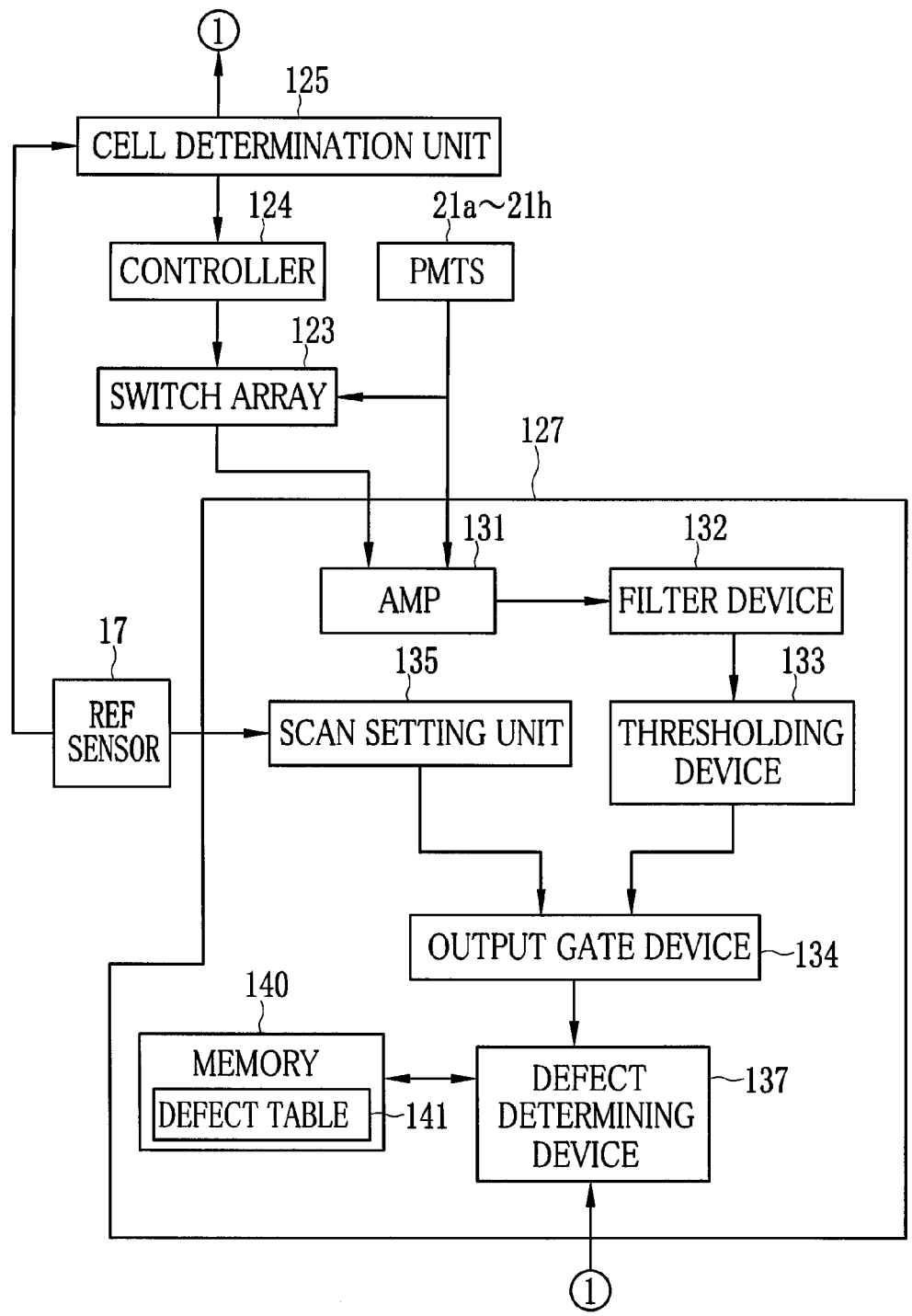
FIG. 18 is a block diagram schematically illustrating defect detector.

In FIG. 18, an amplifier 131 in the defect detector 127 is supplied with output signals (sensor output signals) from the photomultiplier tubes 21a-21h. Among those, an output signal from the photomultiplier tubes 21d is input to the amplifier 131 through the switch array 123. The amplifier 131 amplifies the sensor output signal. A filter device 132 is supplied with the amplified output signal. The filter device 132 includes a band pass filter, and eliminates noise signals of low and high frequency superimposed on the output signal. A thresholding device 133 is supplied with the output signal after elimination of the noise signals. The thresholding device 133 binarizes the output signal into an abnormal output signal with a higher output level than a threshold, and a normal output signal with a lower output level than the threshold. An output gate device 134 for selection is supplied with the abnormal output signal and the normal output signal. The abnormal output signal includes reception light amount information and position information.

A scan setting unit 135 generates an in-place signal. A defect determining device 137 is connected with the output gate device 134. The output gate device 134 determines whether an abnormal output signal should be output to the defect determining device 137 according to whether the in-place signal is input from the scan setting unit 135 or not. The defect determining device 137 is supplied with location information of one of the photomultiplier tubes 21d of entry of the normally transmitted laser beam 103a according to arithmetic operation in the cell determination unit 125.

The defect determining device 137 determines presence of a defect on the film sample 5 according to whether an abnormal output signal is input or not. There are differences in a type, size and location (specific information) according to location information of entry of a main output beam, light amount information of a light amount and location information included in the abnormal output signal (which are referred to as defect feature information). A memory 140 stores plural defect data for defect features (defect feature information) different from one another. There is a defect table 141 in which the defect data are classified for specific information discretely.

The operation of the embodiment is described. The cell determination unit 125 arithmetically determines one of the photomultiplier tubes 21d where the normally transmitted laser beam 103a is incident according to a scan speed of the detection laser beam 3 and time elapsed from an input of the passage signal, and supplies the defect determining device 137 with the location information of a main output beam. In FIG. 16, the detection laser beam 3 becomes incident on a first one of the photomultiplier tubes 21d as counted in the leftward direction at time t1. The detection laser beam 3 becomes incident on a second one of the photomultiplier tubes 21d as counted in the leftward direction at time t2. At time t3, the detection laser beam 3 is transmitted through the film sample 5, and becomes incident on a third one of the photomultiplier tubes 21d as counted in the leftward direction. Similarly, the detection laser beam 3 becomes incident on fourth to 22nd ones of the photomultiplier tubes 21d as counted in the leftward direction at times t4-t22. The detection laser beam 3 becomes incident on 23rd and 24th ones of the photomultiplier tubes 21d as counted in the leftward direction at times t23 and t24.

Figure 19A:
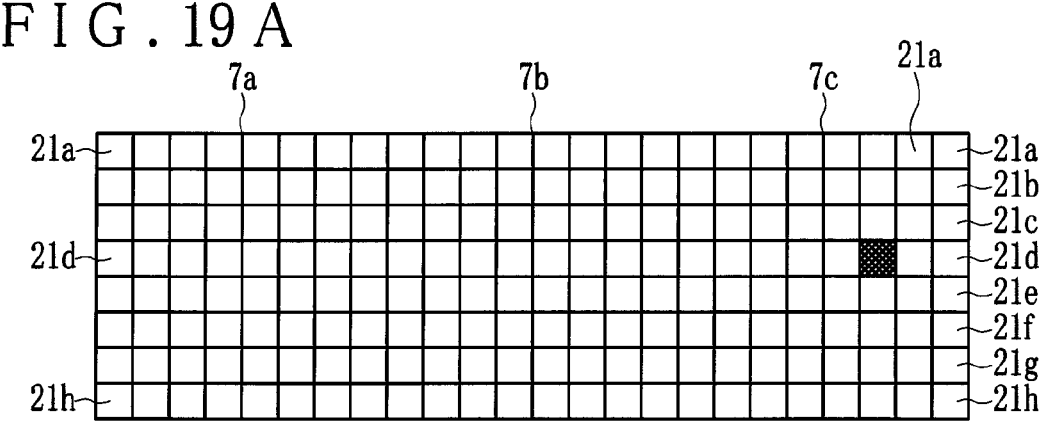
FIGS. 19A-19D are explanatory views in a plan illustrating the light receivers in a state of switching photomultiplier tubes.
Figure 19B:
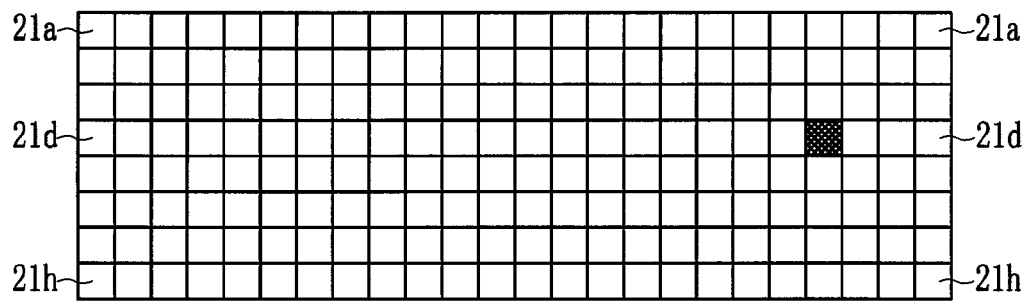
Figure 19C:
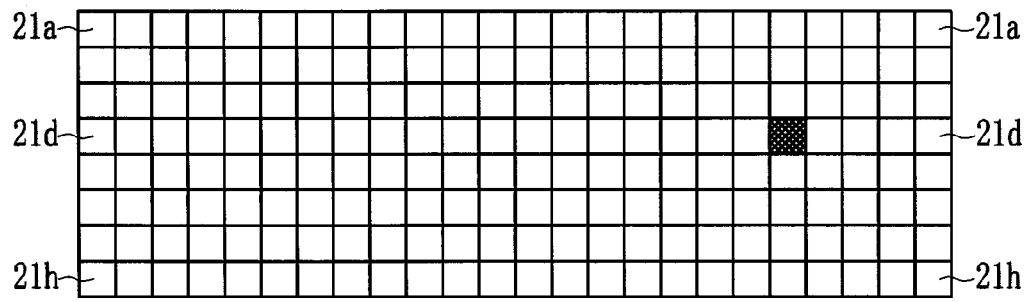
Figure 19D:
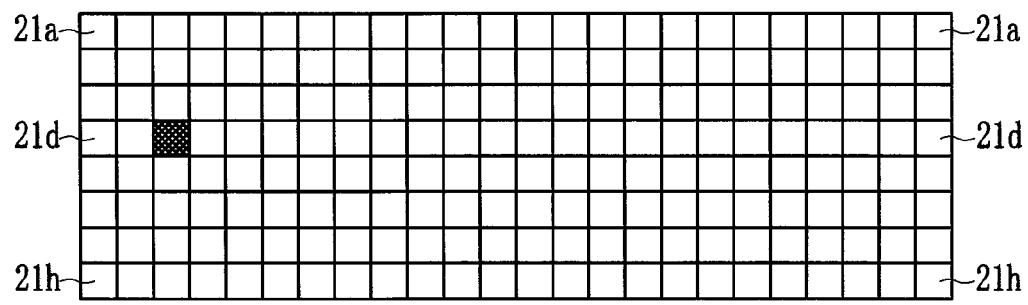

The controller 124 selectively turns off the switch elements 123a connected with one of the photomultiplier tubes 21d arithmetically determined by the cell determination unit 125, and turns on the remainder of the switch elements 123a. In FIG. 19A, a state at time t3 from the input of the passage signal is illustrated. One of the switch elements 123a connected with a third one of the photomultiplier tubes 21d (hatched in FIG. 19A) as counted in a direction to the left is turned off. In FIGS. 19B and 19C, states at times t4 and t5 from the input of the passage signal are illustrated. Two of the switch elements 123a connected with fourth and fifth ones of the photomultiplier tubes 21d as counted in the direction to the left are turned off. In FIG. 19D, a state at time t22 from the input of the passage signal is illustrated. One of the switch elements 123a connected with a 22nd one of the photomultiplier tubes 21d as counted in a direction to the left (a third one as counted in a direction to the right) is turned off. In this manner, the photomultiplier tubes 21d at which the switch elements 123a are turned off are changed over in synchronism with scanning of the detection laser beam 3.

In FIG. 15, no defect is present on the film sample 5. The detection laser beam 3 is totally transmitted through the film sample 5 to become the normally transmitted laser beam 103a. Only the normally transmitted laser beam 103a enters the photomultiplier tubes 21a-21h. One of the switch elements 123a connected with one of the photomultiplier tubes 21d upon entry of the normally transmitted laser beam 103a is turned off. An output signal output by the photomultiplier tube 21d is not input to the amplifier 131. No abnormal output signal is input to the defect determining device 137. Thus, the photomultiplier tube 21d where the switch element 123a is turned off is masked electrically. The defect determining device 137 determines that the film sample 5 is free from defects when no abnormal output signal is input.

Figure 20:
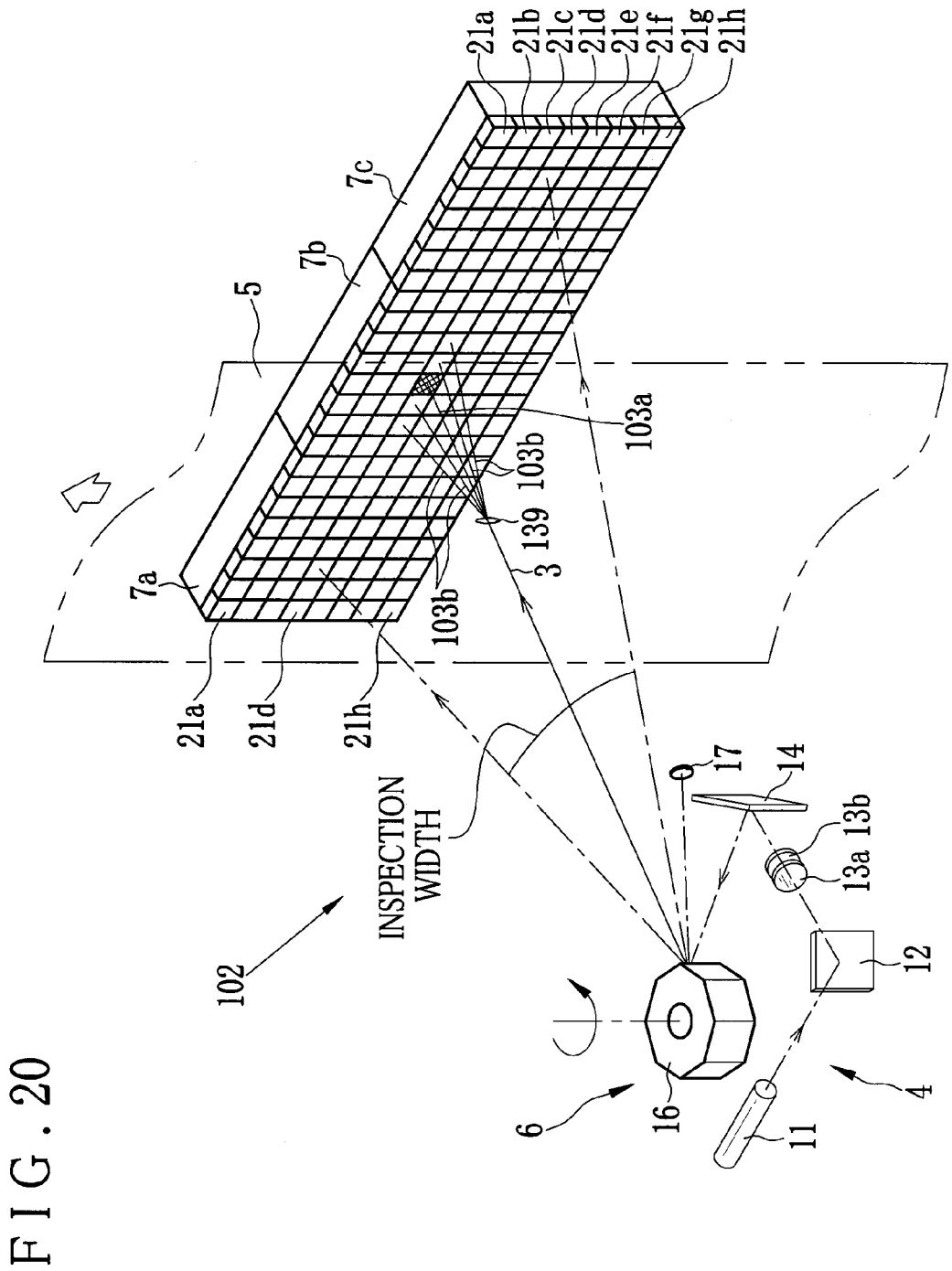
FIG. 20 is a perspective view illustrating the surface inspection apparatus in a state of applying a detection laser beam.

In FIG. 20, a defect 139 is present on the film sample 5, such as a scratch, streak and the like. The detection laser beam 3, upon incidence on the defect 139, becomes the normally transmitted laser beam 103a and scattered light 103b scattered by the defect 139. The scattered light 103b becomes incident on a number of surrounding cells disposed close to the photomultiplier tubes 21d (hatched in FIG. 20) where the normally transmitted laser beam 103a is incident.

The photomultiplier tubes 21d where the scattered light 103b is incident generate an output signal, which is constituted by light amount information and location information. As the switch elements 123a are turned on at one or more of the photomultiplier tubes 21d of entry of the scattered light 103b, the sensor output signal is input to the amplifier 131 through the switch elements 123a. The amplifier 131 amplifies the output signal and outputs this to the filter device 132. As one of the switch elements 123a is turned off at one of the photomultiplier tubes 21d of entry of the normally transmitted laser beam 103a, no output signal is input to the amplifier 131. No abnormal output signal is input to the defect determining device 137.

The filter device 132 eliminates noise components from the output signal, and then outputs this to the thresholding device 133. The thresholding device 133 binarizes the output signal to generate an abnormal output signal with a higher output level than the threshold and a normal output signal with a lower output level than the threshold. Those are supplied to the output gate device 134.

While the in-place signal is input, the output gate device 134 outputs the abnormal output signal to the defect determining device 137. While no in-place signal is input, the output gate device 134 does not output an abnormal output signal to the defect determining device 137.

The defect determining device 137, upon receiving the abnormal output signal, determines presence of a defect on the film sample 5, and refers to the defect table 141 to retrieve defect data among the plural defect data in association with the specific information classified according to the input specific information.

An output signal output by the photomultiplier tubes 21d upon incidence of the normally transmitted laser beam 103a is not input to the amplifier 131. An abnormal output signal is not input to the defect determining device 137. Thus, the defect determining device 137 can process the abnormal output signal consecutively. The construction of the defect determining device 137 can be much simpler than a structure in which an abnormal output signal according to an output signal output by the photomultiplier tube receiving a main output beam is eliminated after inputting to a defect determining device.

An output signal from one of the photomultiplier tubes 21d of entry of the normally transmitted laser beam 103a is not used for performing tasks of detecting a defect, and determining a type, size and location of a defect. Thus, the output signal from a photomultiplier tube of entry of a main output beam can have higher precision than an output signal for use in the detection and determination. It is possible to detect the defect 139 even in a finer form than a conspicuous defect, such as a sharp or finely retracting stripe or the like.

Figure 21:
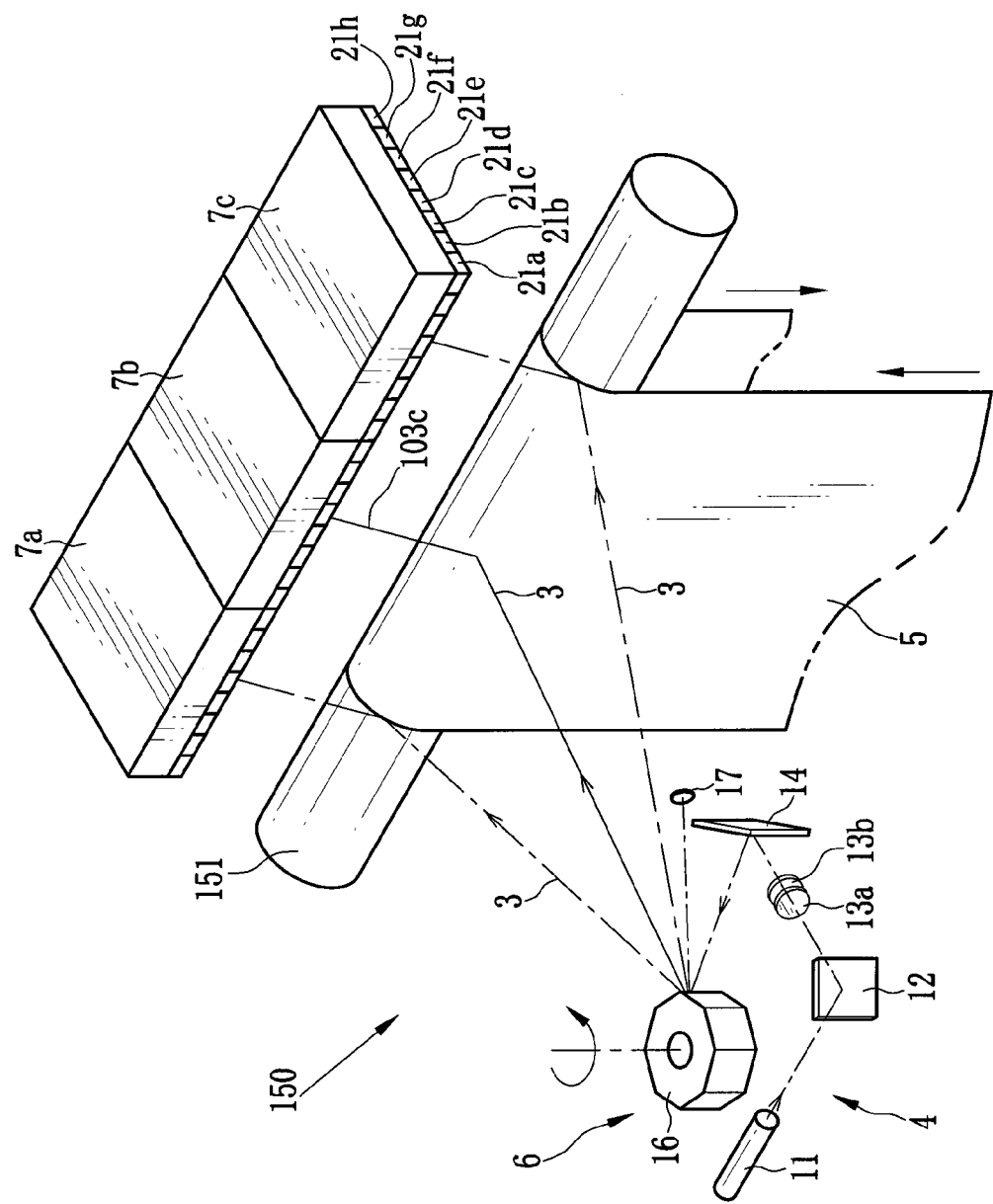
FIG. 21 is a perspective view illustrating still another preferred surface inspection apparatus of a reflection type.
Figure 22:
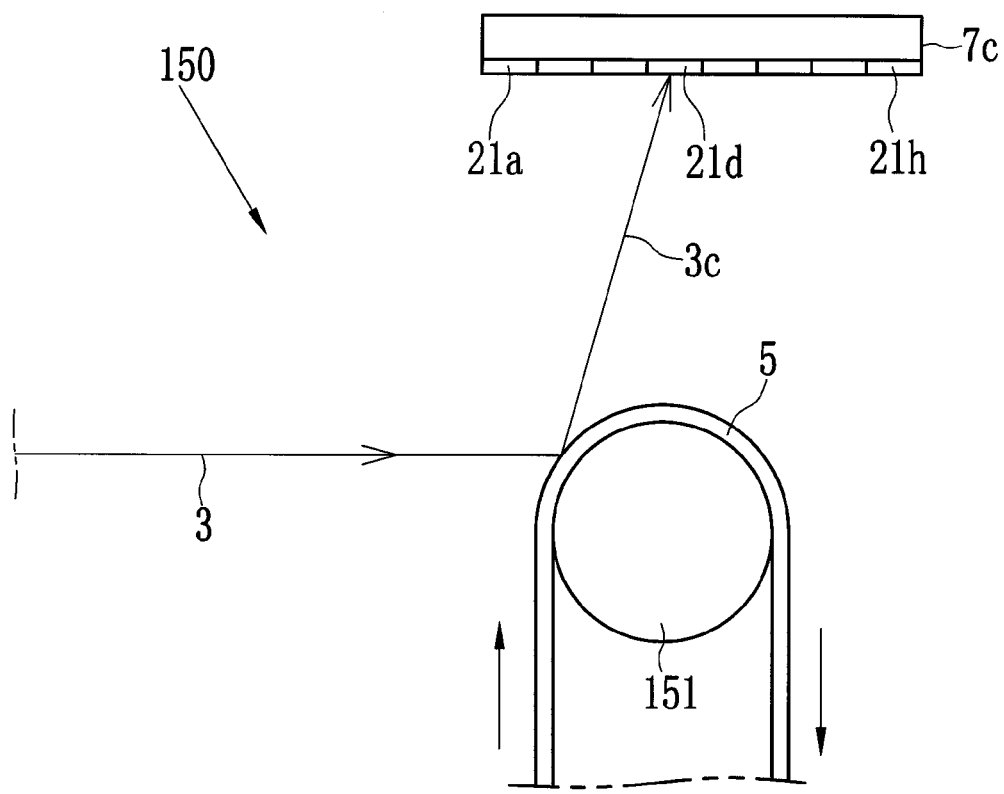
FIG. 22 is a side elevation illustrating the surface inspection apparatus.

In FIGS. 21 and 22, still another preferred surface inspection apparatus 150 is illustrated, in which a beam is reflected on the film sample 5. Elements similar to those of the embodiment are designated with identical reference numerals. A support roller 151 contacts and transports the film sample 5. A rolled portion of the film sample 5 at the support roller 151 receives application of the detection laser beam 3. The light receivers 7a-7c are disposed higher than the support roller 151. A normally reflected laser beam 103c travels from the film sample 5 after reflection on the film sample 5. The photomultiplier tubes 21d are disposed for receiving the normally reflected laser beam 103c. The cell determination unit 125 arithmetically determines one of the photomultiplier tubes 21d for entry of the normally reflected laser beam 103c among the photomultiplier tubes 21d of the fourth array. The controller 124 turns off one of the switch elements 123a in connection with the determined one of the photomultiplier tubes 21d, and turns on the remainder of the switch elements 123a. Tasks of processing an output signal from the photomultiplier tubes 21a-21h and detecting defects are performed in a manner similar to the above embodiments.

In the embodiment, a particular switch is turned off to prevent supply of an output signal to a defect detector after output from the photomultiplier tube of entry of a main output beam. Furthermore, it is possible to turn off a switch to lower the sensitivity of the photomultiplier tube of entry of a main output beam by control of electric masking. The main output beam is prevented from reception so as to suppress reception of an output signal in the defect detector.

Also, sensitivity of photomultiplier tubes disposed to surround the photomultiplier tube of entry of a main output beam can be set higher in synchronism with scanning of a laser beam for the purpose of controlling plural photomultiplier tubes.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. A surface inspection apparatus comprising:
a light source for applying a detection beam to a sample of a film form;
a light receiver, having plural photoelectric cells arranged in a width direction of said sample, for receiving output light transmitted or reflected by said sample;
a defect detector for detecting a defect on said sample according to an output signal output by each of said photoelectric cells; and
a sensitivity corrector for correcting sensitivity of said photoelectric cells,
wherein said sensitivity corrector is constituted by plural sensitivity correctors for correcting sensitivity of respectively one of said photoelectric cells corresponding thereto, to keep a signal difference of said output signal between said photoelectric cells as small as a predetermined value or less, and
wherein said sensitivity corrector includes:
plural light valves each of which is disposed upstream of one of said photoelectric cells; and
a transmission control unit for setting transmittance of said light valves by applying voltage thereto.

2. A surface inspection apparatus as defined in claim 1, wherein said sample is elongated, and said defect is detected while said sample travels continuously.

3. A surface inspection apparatus as defined in claim 1, wherein said photoelectric cells in said light receivers are arranged in a longitudinal direction of said sample in addition to said width direction and positioned in a matrix form.

4. A surface inspection apparatus as defined in claim 3, wherein said photoelectric cells are photomultiplier tubes.

5. A surface inspection apparatus, comprising:
a light source for applying a detection beam to a sample of a film form;
a light receiver, having plural photoelectric cells arranged in a width direction of said sample, for receiving output light transmitted or reflected by said sample;
a defect detector for detecting a defect on said sample according to an output signal output by each of said photoelectric cells; and
a sensitivity corrector for correcting sensitivity of said photoelectric cells,
wherein said sensitivity corrector is constituted by plural sensitivity correctors for correcting sensitivity of respectively one of said photoelectric cells corresponding thereto, to keep a signal difference of said output signal between said photoelectric cells as small as a predetermined value or less, and
wherein each of said sensitivity correctors is an optical filter disposed upstream of one of said photoelectric cells, for adjusting an amount of said output light being transmitted.

6. A surface inspection apparatus as defined in claim 1, wherein each of said sensitivity correctors has an amplifier for amplifying said output signal of one of said photoelectric cells associated therewith.

7. A surface inspection apparatus as defined in claim 1, wherein said predetermined value is equal to or less than 15%.

8. A surface inspection apparatus as defined in claim 7, wherein said predetermined value is equal to or less than 5%.

9. A surface inspection apparatus, comprising:
a light source for applying a detection beam to a sample of a film form;
a light receiver, having plural photoelectric cells arranged in a width direction of said sample, for receiving output light transmitted or reflected by said sample;

a defect detector for detecting a defect on said sample according to an output signal output by each of said photoelectric cells; and a sensitivity corrector for correcting sensitivity of said photoelectric cells, wherein said sensitivity corrector is constituted by plural sensitivity correctors for correcting sensitivity of respectively one of said photoelectric cells corresponding thereto, to keep a signal difference of said output signal between said photoelectric cells as small as a predetermined value or less, wherein said sample is elongated, and said defect is detected while said sample travels continuously, wherein said light receiver is constituted by a plurality of light receivers arranged on an arcuate curved line defined about a point where said detection beam is incident on said sample, and wherein said plural light receivers are arranged in a zigzag form with reference to said arcuate curved line.

10. A surface inspection apparatus as defined in claim 2, wherein said light source includes:
a light source device for generating detection light;
an optical system for condensing said detection light to create said detection beam of a spot shape; and
a beam scanning device for directing said detection beam in said width direction of said sample for scanning.

11. A surface inspection apparatus as defined in claim 2, wherein said light source includes:
a light source device for generating detection light;
an optical system for condensing said detection light to create said detection beam of a linear shape extending in said width direction of said sample.

12. A surface inspection apparatus as defined in claim 10, further comprising a masking processor, supplied with said output signal output by respectively said photoelectric cells, for eliminating an output signal of a first photoelectric cell among said photoelectric cells from detection processing in said defect detector, said first photoelectric cell being disposed to receive entry of a main output beam obtained by normally transmitting or reflecting said detection beam on said sample.

13. A surface inspection apparatus as defined in claim 12, wherein said masking processor includes:
a cell determination unit for determining a location of said first photoelectric cell among said photoelectric cells according to start time of scanning of said detection beam with said beam scanning device;
a switching device for turning on and off said output signal from said first photoelectric cell to said defect detector.

14. A surface inspection method comprising steps of:
applying a detection beam to a sample of a film form;
directing said detection beam in a width direction of said sample for scanning;
selectively switching on and off photoelectric cells in synchronism with scanning of said detection beam, said photoelectric cells being arranged in said width direction of said sample, for receiving output light transmitted or reflected by said sample; and
detecting a defect on said sample according to an output signal output by one of said photoelectric cells being switched on.

15. A surface inspection apparatus comprising:
a light source for applying a detection beam to a sample of a film form;
a beam scanning device for directing said detection beam in a width direction of said sample for scanning;
a light receiver, having plural photoelectric cells arranged in said width direction of said sample, for receiving output light transmitted or reflected by said sample;
a masking processor, supplied with an output signal output by respectively said photoelectric cells, for eliminating an output signal of a first photoelectric cell among said photoelectric cells from detection processing, said first photoelectric cell being disposed to receive entry of a main output beam obtained by normally transmitting or reflecting said detection beam on said sample, wherein said masking processor includes a switching device for turning on and off said output signal from said first photoelectric cell to said defect detector; and
a defect detector for detecting a defect on said sample according to said output signal output by one of said photoelectric cells being switched on.

* * * * *